(12) United States Patent
Nelson et al.

(10) Patent No.: US 12,020,818 B1
(45) Date of Patent: Jun. 25, 2024

(54) CROSS CARE MATRIX BASED CARE GIVING INTELLIGENCE

(71) Applicant: SimpleC, LLC, Atlanta, GA (US)

(72) Inventors: Douglas Nelson, Atlanta, GA (US); Daniel V. Pompilio, III, Smyna, GA (US)

(73) Assignee: SimpleC, LLC, Marietta, GA (US)

(*) Notice: Subject to any disclaimer, the term of this patent is extended or adjusted under 35 U.S.C. 154(b) by 204 days.

(21) Appl. No.: 17/832,744

(22) Filed: Jun. 6, 2022

Related U.S. Application Data

(63) Continuation of application No. 15/837,450, filed on Dec. 11, 2017, now Pat. No. 11,355,239.

(60) Provisional application No. 62/432,801, filed on Dec. 12, 2016.

(51) Int. Cl.
| | |
|---|---|
| *G16H 50/20* | (2018.01) |
| *A63B 24/00* | (2006.01) |
| *G06N 5/04* | (2023.01) |
| *G06N 20/00* | (2019.01) |
| *G09B 19/00* | (2006.01) |
| *G16H 10/20* | (2018.01) |
| *G16H 20/30* | (2018.01) |
| *G16H 50/50* | (2018.01) |
| *G16H 50/70* | (2018.01) |

(52) U.S. Cl.
CPC ......... *G16H 50/20* (2018.01); *A63B 24/0075* (2013.01); *G06N 5/04* (2013.01); *G06N 20/00* (2019.01); *G09B 19/00* (2013.01); *G16H 10/20* (2018.01); *G16H 20/30* (2018.01); *G16H 50/50* (2018.01); *G16H 50/70* (2018.01)

(58) Field of Classification Search
CPC ........ G16H 50/20; G16H 50/50; G16H 50/70; G16H 20/30; G16H 10/20; G06N 20/00; G06N 5/04; A63B 24/00; A63B 24/0075; G09B 19/00
See application file for complete search history.

(56) References Cited

U.S. PATENT DOCUMENTS

| | | | |
|---|---|---|---|
| 2009/0177495 A1 | 6/2009 | Abousy et al. | |
| 2012/0078601 A1 | 3/2012 | Avinash et al. | |
| 2015/0019241 A1 | 1/2015 | Bennett et al. | |
| 2017/0262614 A1 | 9/2017 | Vishnubhatla et al. | |

*Primary Examiner* — Timothy A Musselman
(74) *Attorney, Agent, or Firm* — The Webb Law Firm

(57) ABSTRACT

Automating patient care by training an artificial intelligence using a data structure organized in a patient care matrix comprising levels of domain knowledge. The care matrix data structure is defined and populated with training data. The artificial intelligence includes a plurality of artificial intelligence nodes each trained using aspects of the care matrix data structure such that an entity AI node instance is trained using a data set comprising subset of training data utilized in training child entities node instances of the entity AI node being trained. A long form description of a patients behavior or disorder is obtained and a natural language processor is employed to generate input phrases to be supplied to the AI for analysis. The AI analyzes the obtained phrases using a plurality of the trained AI node instances to automatically generate a patient treatment profile including one or more therapies and associated measures.

20 Claims, 17 Drawing Sheets

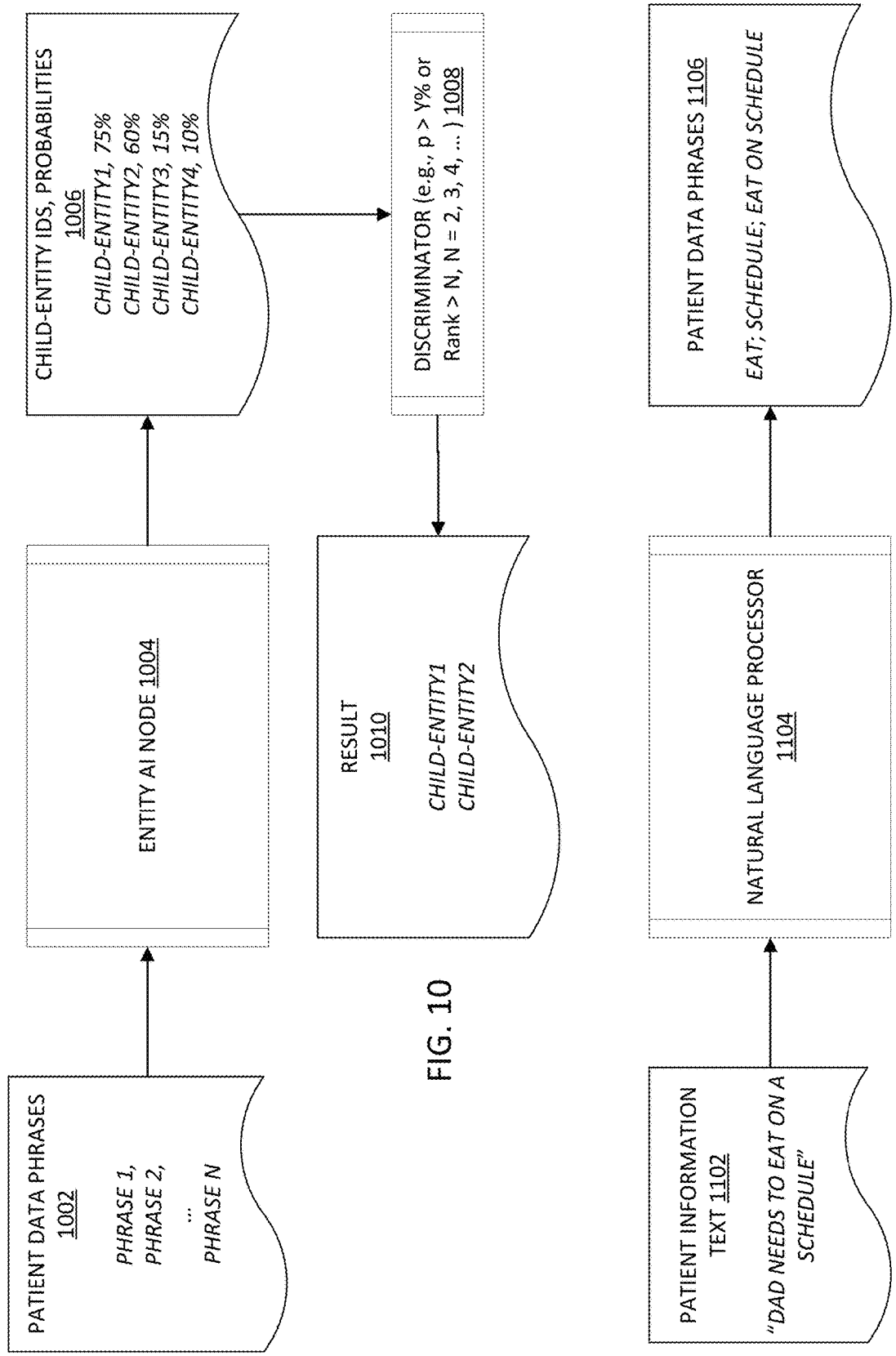

CROSS CARE MATRIX BASED CARE GIVING INTELLIGENCE

CROSS-REFERENCE TO RELATED APPLICATION

This application is a continuation application of U.S. patent application Ser. No. 15/837,450, filed Dec. 11, 2017, which claims priority to U.S. Provisional Patent Application No. 62/432,801, filed Dec. 12, 2016, entitled "SYSTEMS AND METHODS FOR PROVIDING HEALTHCARE VIA A CARE MATRIX PROCESS," both of which are incorporated herein by reference in their entireties.

TECHNICAL FIELD

The technology described herein relates to medical care automation.

BACKGROUND

Traditional patient care develops through person to person interactions. For example, a care specialist, such as a nurse, doctor, psychologist, or social worker may interview a patient exhibiting symptoms of one or more disorders, such as an injury, an illness, a disability, or a disease. The purpose of such an interview is to gather information, or data, in order to capture a description of the individual in terms of their disorder. Such a description may be collected and organized in various ways, such as in physical documents or in one or more data structures stored in a data store associated with one or more computing devices. From this collection of information, a care specialist may identify one or more treatments for a patient to improve the patients quality of life or to attempt to cure one or more aspects of a patients disorder.

Because patient care has historically been organized around this human to human dynamic, each interaction is heavily influenced by the experience and training of the care specialist. For example, a care specialist interviews such a patient largely based on the care specialist's personal experience, specific training, and personal opinions or intuitions about what sort of treatment works to address the symptoms expressed by the patient. Therefore, any number of specialists may interview a patient and each of those specialists may ultimately obtain different information, in different forms, and identify different therapies for the same single patient. Also, this traditional human to human dynamic has a high cost by requiring a great deal of time for a care specialist to interview a patient, gather and develop information about the patient, and then to analyze the information to identify therapies. While being subject to great variability and requiring great time and cost, the historic human to human interaction between patient and care specialist is prone to error.

Attempts at automating patient care using traditional computer algorithms are prohibitively complicated, because the problems addressed by care specialist are not well suited to solving by known computer algorithms such as key word searching, decision trees, etc.

SUMMARY

In an embodiments interrelated with the other embodiments disclosed herein, a patient is automatically treated. The patient has a disorder associated with a first domain of symptoms exhibited by members of a population of patients having the disorder. Treating the patient includes training an artificial intelligence (AI) to obtain a trained AI capable of generating a treatment profile for one or more of the members of the population responsive to a set of input phrases. Training the AI includes receiving a set of first symptom training phrase associations comprising a plurality of first symptom training phrases each associated with one of a plurality of first symptom treatment goals each of the first symptom treatment goals associated with one or more first therapies for treating a first symptom. And, training the AI includes receiving a set of second symptom training phrase associations comprising a plurality of second symptom training phrases each associated with one of a plurality of second symptom treatment goals each of the second symptom treatment goals associated with one or more second therapies for treating a second symptom. And, training the AI includes receiving a set of first domain training phrase associations including: (i) the plurality of first symptom training phrases each associated with the first symptom and (ii) the plurality of second symptom training phrases associated with the second symptom. And, training the AI includes training a first AI node instance with the set of first domain training phrase associations to obtain a first domain AI node capable of generating, responsive to the set of input phrases, a first set of symptoms to be treated comprising: the first symptom or the second symptom; and one or more symptom scores, each respective symptom score representative of a strength of a relationship between each of one or more symptom to be treated and the set of input phrases. And, training the AI includes training a second AI node instance with the set of first symptom training phrase associations to obtain a first symptom AI node capable of generating, responsive to the set of input phrases, a first set of proposed symptom treatment goals comprising: one or more of the plurality of first symptom treatment goals; and one or more first symptom goal scores, each respective first symptom goal score representative of a strength of a relationship between each one of the one or more first symptom treatment goals and the set of input phrases. And, training the AI includes training a third AI node instance with the set of second symptom training phrase associations to obtain a second symptom AI node instance capable of generating, responsive to the set of input phrases, a second set of proposed symptom treatment goals comprising: one or more of the plurality of second symptom treatment goals; and one or more second symptom goal scores, each respective second symptom goal score representative of a strength of a relationship between each of the one of the one or more second symptom treatment goals and the set of input phrases. Automatically treating a patient further includes generating, using the trained AI, a treatment profile of the patient including one or more therapies to be performed to treat a current state of the patient the current state associated with the disorder by obtaining a description of the current state of the patient, and then generating, using a natural language processor, a first set of input phrases based on the description of the current state of the patient. Automatically treating a patient further includes querying the trained AI to obtain using the first set of input phrases as the set on input phrases. Querying the trained AI includes providing the first set of input phrases to the first domain AI node, and returning, responsive to providing the first set of input phrases to the first domain AI node, the first symptom and the second symptom. Querying the trained AI also includes providing the first set of input phrases to the first symptom AI node and returning, from the first symptom AI node responsive to providing the first set of input phrases to the first symptom AI node: the first set of proposed symptom treatment goals including a first goal and a second goal; a first score associated with the first goal; and a second score associated with the second goal. Querying the trained AI also includes providing the first set of input phrases to the second symptom AI node, and returning, from the second symptom AI node responsive to providing the first set of input phrases to the second symptom AI node: the second set of proposed symptom treatment goals including the first goal and a third goal; a third score associated with the first goal; and a fourth score associated with the third goal. Then, the first score and the third score are aggregated to obtain an aggregated score and associating the aggregated score with the first goal. Then, the first goal and the third goal are selected when the aggregated score and the fourth score exceed a goal weight threshold and omitting the second goal when the second score does not exceed the threshold. Then the treatment profile is generated to include one or more first therapies associated with the first goal and one or third therapies associated with the third goal. Finally, the treatment profile is provided to the patient or the patient's caregiver.

In an embodiments interrelated with the other embodiments disclosed herein, an artificial intelligence (AI) instance is trained to treat a plurality of patients each having one of a plurality of disorders each respectively associated with at least one of a plurality domain of symptoms exhibited by members of a population of patients having the disorder by defining care matrix data structure for use in training the AI. Defining a care matrix data structure includes defining a set of domain data structures, each domain structure associated with a population of patients exhibiting one or more of a plurality of related symptoms. And, defining a care matrix data structure includes defining a set of symptom data structures, each symptom data structure associated with (i) one of a plurality of symptoms exhibited by patients within one or more domains and (ii) one or more goals for managing the one of a plurality of symptoms. And, defining a care matrix data structure includes defining a set of goal data structures, each goal data structure associated with (i) one of the one or more goals and (ii) one or more therapies for managing a symptom associated with the one of the one or more goals. And, defining a care matrix data structure includes defining a set of therapy data structures, each therapy data structure describing a therapy treatment associated with one or more of the goal data structures. The care matrix data structure is defined such that each of two or more of the domain data structures respectively include a reference to one of two or more distinct sets of domain training data, further wherein each of two or more of the symptom data structures respectively include a reference to one of two or more distinct sets of symptom training data, further wherein each of two or more of the goal data structures respectively include a reference to one of two or more distinct sets of goal training data. The care matrix data structure is further defined for use in training an AI instance to obtain a trained treatment AI capable of generating, responsive to a description of a patient's current state, a patient therapy profile, the patient therapy profile including one or more therapies for treating one or more symptoms identified by the AI based on the description of the patient's current state.

In an embodiments interrelated with the other embodiments disclosed herein, an artificial intelligence (AI) is trained in order to obtain a trained AI capable of generating a treatment profile for one or more members of a population responsive to a set of input phrases. The AI is trained by first generating a set of first symptom training phrase associations comprising a plurality of first symptom training phrases each associated with one of a plurality of first symptom treatment goals each of the first symptom treatment goals associated with one or more first therapies for treating a first symptom. And, the AI is trained by generating a set of second symptom training phrase associations comprising a plurality of second symptom training phrases each associated with one of a plurality of second symptom treatment goals each of the second symptom treatment goals associated with one or more second therapies for treating a second symptom. And, the AI is trained by generating a set of first domain training phrase associations including: (i) the plurality of first symptom training phrases each associated with the first symptom and (ii) the plurality of second symptom training phrases associated with the second symptom. And, the AI is trained by training a first AI node instance with the set of first domain training phrase associations to obtain a first domain AI node capable of generating, responsive to the set of input phrases, a first set of symptoms to be treated comprising: the first symptom or the second symptom; and one or more symptom scores, each respective symptom score representative of a strength of a relationship between each of one or more symptom to be treated and the set of input phrases. And, the AI is trained by training a second AI node instance with the set of first symptom training phrase associations to obtain a first symptom AI node capable of generating, responsive to the set of input phrases, a first set of proposed symptom treatment goals comprising: one or more of the plurality of first symptom treatment goals; and one or more first symptom goal scores, each respective first symptom goal score representative of a strength of a relationship between each one of the one or more first symptom treatment goals and the set of input phrases. And, the AI is trained by training a third AI node instance with the set of second symptom training phrase associations to obtain a second symptom AI node instance capable of generating, responsive to the set of input phrases, a second set of proposed symptom treatment goals comprising: one or more of the plurality of second symptom treatment goals; and one or more second symptom goal scores, each respective second symptom goal score representative of a strength of a relationship between each of the one of the one or more second symptom treatment goals and the set of input phrases.

In an embodiments interrelated with the other embodiments disclosed herein, a trained AI automatically generates a treatment profile for a patient that is a member of a domain. The treatment profile includes one or more therapies to be performed to treat aspects of a current state of the patient associated with a disorder of the patient. The AI automatically generates a treatment profile by obtaining a description of the current state of the patient's disorder, and then generating a first set of input phrases based on the description of the current state of the patient using a natural language processor. Then, trained AI is queried using the first set of input phrases as the set on input phrases, wherein querying the trained AI comprises first providing the first set of input phrases to the first domain AI node. Then, returning, responsive to providing the first set of input phrases to the first domain AI node, the first symptom and the second symptom. Then providing the first set of input phrases to the first symptom AI node and returning, from the first symptom AI node responsive to providing the first set of input phrases to the first symptom AI node: the first set of proposed symptom treatment goals including a first goal and a second goal; a first score associated with the first goal; and a second score associated with the second goal. Then, querying the AI continues by providing the first set of input phrases to the second symptom AI node and returning, from the second symptom AI node responsive to providing the first set of input phrases to the second symptom AI node: the second set of proposed symptom treatment goals including the first goal and a third goal; a third score associated with the first goal; and a fourth score associated with the third goal. Then the first score and the third score are aggregated to obtain an aggregated score the aggregated score is associated with the first goal. The first goal and the third goal are selected when the aggregated score and the fourth score exceed a goal weight threshold and the second goal is omitted when the second score does not exceed the threshold. Lastly, the treatment profile is generated to include one or more first therapies associated with the first goal and one or third therapies associated with the third goal and provided to the patient or the patients caregiver.

In an embodiments interrelated with the other embodiments disclosed herein, an automated patient care system includes one or more data stores configured to store training data in an AI training data structure, and patient data in an AI query structure. The system also includes a natural language processing engine, an interface for obtaining the patient data in the form of a description of the current state of the patient, and an artificial intelligence (AI) training engine stored on a non-transitory computer-readable medium and executable by a processor. The AI training engine configured to train an AI to obtain a trained AI capable of generating a treatment profile for one or more of the members of the population responsive to a set of input phrases. The AI training includes generating a set of first symptom training phrase associations comprising a plurality of first symptom training phrases each associated with one of a plurality of first symptom treatment goals each of the first symptom treatment goals associated with one or more first therapies for treating a first symptom. The AI training also includes generating a set of second symptom training phrase associations comprising a plurality of second symptom training phrases each associated with one of a plurality of second symptom treatment goals each of the second symptom treatment goals associated with one or more second therapies for treating a second symptom. The AI training also includes generating a set of first domain training phrase associations including: (i) the plurality of first symptom training phrases each associated with the first symptom and (ii) the plurality of second symptom training phrases associated with the second symptom. The AI training also includes training a first AI node instance with the set of first domain training phrase associations to obtain a first domain AI node capable of generating, responsive to the set of input phrases, a first set of symptoms to be treated comprising: the first symptom or the second symptom; and one or more symptom scores, each respective symptom score representative of a strength of a relationship between each of one or more symptom to be treated and the set of input phrases. The AI training also includes training a second AI node instance with the set of first symptom training phrase associations to obtain a first symptom AI node capable of generating, responsive to the set of input phrases, a first set of proposed symptom treatment goals comprising: one or more of the plurality of first symptom treatment goals; and one or more first symptom goal scores, each respective first symptom goal score representative of a strength of a relationship between each one of the one or more first symptom treatment goals and the set of input phrases. The AI training also includes training a third AI node instance with the set of second symptom training phrase associations to obtain a second symptom AI node instance capable of generating, responsive to the set of input phrases, a second set of proposed symptom treatment goals comprising: one or more of the plurality of second symptom treatment goals; and one or more second symptom goal scores, each respective second symptom goal score representative of a strength of a relationship between each of the one of the one or more second symptom treatment goals and the set of input phrases. The system further includes a patient therapy profile generation engine, including the trained AI, stored on a non-transitory computer-readable medium and executable by a processor. The patient therapy profile generation engine is configured to generate, using the trained AI, a treatment profile of the patient including one or more therapies to be performed to treat a current state of the patient the current state associated with the disorder by obtaining the description of the current state of the patient. The patient therapy profile generation engine is further configured to generate, using a natural language processor, a first set of input phrases based on the description of the current state of the patient. The patient therapy profile generation engine is further configured to query the trained AI to obtain using the first set of input phrases as the set on input phrases. Querying the trained AI includes providing the first set of input phrases to the first domain AI node and returning, responsive to providing the first set of input phrases to the first domain AI node, the first symptom and the second symptom. Querying the trained AI also includes providing the first set of input phrases to the first symptom AI node and returning, from the first symptom AI node responsive to providing the first set of input phrases to the first symptom AI node: the first set of proposed symptom treatment goals including a first goal and a second goal; a first score associated with the first goal; and a second score associated with the second goal. Querying the trained AI also includes providing the first set of input phrases to the second symptom AI node, and returning, from the second symptom AI node responsive to providing the first set of input phrases to the second symptom AI node: the second set of proposed symptom treatment goals including the first goal and a third goal; a third score associated with the first goal; and a fourth score associated with the third goal. And, generating a treatment profile of the patient using the trained AI also includes aggregating the first score and the third score to obtain an aggregated score and associating the aggregated score with the first goal; and selecting the first goal and the third goal when the aggregated score and the fourth score exceed a goal weight threshold and omitting the second goal when the second score does not exceed the threshold; and generating the treatment profile including one or more first therapies associated with the first goal and one or third therapies associated with the third goal; and providing the treatment profile to the patient or the patients caregiver.

BRIEF DESCRIPTION OF THE DRAWINGS

FIG. 10 illustrates a block diagram of an example system for obtaining results responsive to an input to an entity AI node entity in accordance with various embodiments.

FIG. 11 illustrates a block diagram of an example system for obtaining results of an natural language processor responsive to an input in accordance with various embodiments.

DETAILED DESCRIPTION

Figure 1:
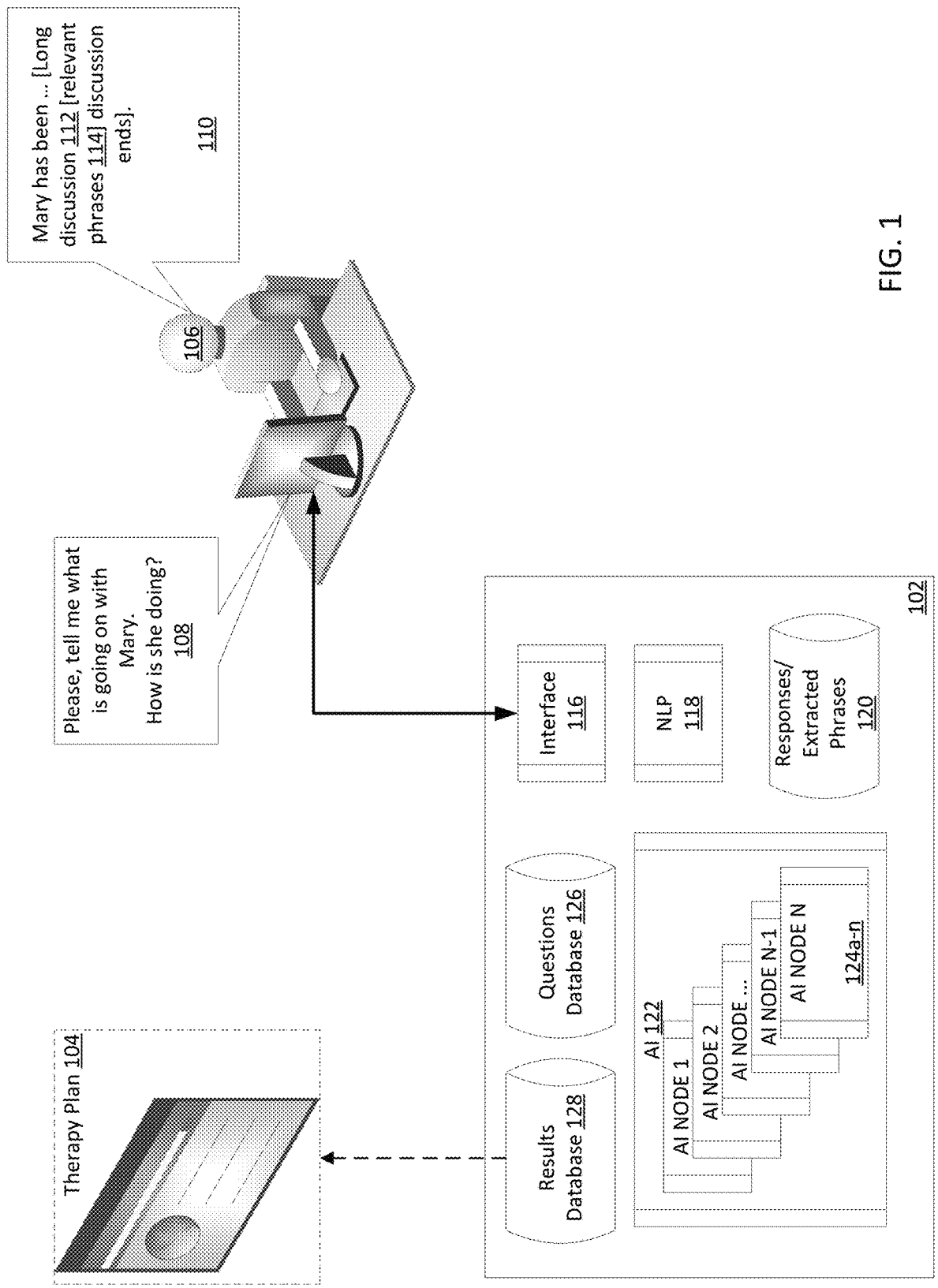
FIG. 1 illustrates an exemplary system for providing automated medical care to various populations of patients in accordance with various embodiments.

Systems and methods as described herein provide a mechanism for training an artificial intelligence to provide customized care tailored to the needs of persons having various disorders and exhibiting various behaviors or symptoms associated with particular domains of populations of patients having similar care needs with improved performance over conventional automation systems. Systems and methods as described herein also provide a mechanism for automatically providing patient tailored to the needs of persons having disorders and exhibit behavior and symptoms associated with domains of populations of patients having similar care needs with improved performance over conventional automation systems. Systems and methods as described herein also provide a mechanism for providing consistent automated care for patients through the use of a care matrix.

In a typical medical care environment, a care professional evaluates a patient and develops a care plan for that patient. That care plan may include a number of therapies and corresponding goals. For example, an Alzheimer's patient may be diagnosed and prescribed particular memory drills and physical therapy with the intent to delay memory loss and physical degradation by a doctor. Such a paradigm is problematic in that it is not a scalable process and is not a repeatable process. The process is not scalable in that it requires high-level medical professional judgment for each patient and for each adjustment to that patient's care. The process is further not repeatable because patient data will often be interpreted differently by different medical professionals, such that therapies and goals will differ across patients having matching health statuses.

In standard care settings, based on human to human interactions, whether supported by known automation systems (key word searchers, tree searching, etc.) or not, a care specialist like a psychologist, a nurse, or a social worker would gather data about a patient in order to produce a therapy profile. The care specialist would accomplish this by interviewing, or providing forms, to the patient, and potentially various people associated with the patient, to elicit information. Once the data was gathered, the care specialist would analyze the data and generate the therapy profile. While this process allows exceptional individual care providers to provide exceptional analysis and therapy, five given care specialists typically provide five highly varying analyses and therapy profiles in response to the same set of patient data. Thus, known systems of providing patient care are rarely repeatable and vary in quality greatly. Furthermore, a typical process may require more than 12 hours of an individual care giver's time to perform the analysis and generate the therapy profile. And, the amount of education and experience required by a care specialist in order to provide quality care is high. Therefore, the cost associated with each therapy profile is prohibitively high, while the process itself is unscalable because well trained care specialists are rare and their analysis is necessarily a lengthy process.

Thus, an automated system for evaluating patients based on a patient, or caregivers, natural language responses is desired. Such a system allows for repeatability with consistent results, and simple scalability for example by delivery as a simple software installer or as a software as a service (SaaS) service.

In one embodiment, outcomes are determined based on differences between an initial evaluation of the patient (e.g., the initial patient condition data) and later evaluations, including a final evaluation, of the patient (e.g., based on updates to the patient condition data) to evaluate the effectiveness of the therapies/goals on the patient. For example, an amount of time necessary for the patient to reach an assigned goal, if that assigned goal is met at all, is tracked. Such outcome data is aggregated across multiple patients (e.g., 100s of patients, 1000s of patients) to determine the effectiveness of assigned therapies/goals. The care matrix data structure can be adjusted based on this aggregated data to improve future performance.

In an embodiment, a care goals-based system is implemented as follows. The care matrix data structure identifies domains, care needs, goals, measures, therapies and their relationship to each other. These relationships completely identify what the system treats, how the system treats it, and how the system measure outcomes. The care matrix data structure, in one example, includes one or more of the following levels of entities:

Domain entities: a grouping of one or more care needs common to patients in a particular population, for example patients exhibit common symptoms, or patients seeking treatment for symptoms having related treatment goals. For example, patients having various unrelated disorders may each suffer from sleep deprivation due to an inability to sleep, and so may be treated as members of the same population of patients exhibiting sleep deprivation. This domain level is the top level of the matrix. In another example, a care matrix data structure includes domains of "Memory Care" and "Developmental Disability." In another example, a care matrix data structure includes domains of "Alzheimer's disease" and "PTSD." The relationship between Domain entities and Symptom entities is one to many.

Symptom entities, or Care Needs entities—Care needs, arising from various symptoms, may be shared across domains, or may be unique to a single domain. The relationship between symptom entities to Domain entities one to many. Many symptoms are exhibited by population members of a particular domain. Symptoms such as "lack of sleep" give rise to care needs such as "needs more sleep." To address the care needs associated with an exhibited symptom, a treatment plan profile establishes one or more goals for a patient, and these goals are pursued by performing therapies. Thus, the relationship between each symptom entity and goal, or therapy, entities is one to many.

Care Goals, or simply Goals, entities—a goals entities are groupings of one or more therapies for treating symptoms exhibited by population member patients of a particular domain. Thus the relationship between each goal entity and each symptom entity is one to many. Care goals like symptoms are shared across domains, and the relationships between a care goal and two or more domains may differ based on the extent to which population members of a domain exhibit related symptoms that cause presenting patients to seek to achieve similar goals. A care goal is associated with a specific symptom, and is something the system seeks to accomplish with the patient in order to alleviate, medicate, mediate, or manage a particular symptom, or address a care need.

Care Activities, or simply Therapies, entities—therapy entities include one or more therapies for accomplishing one or more goals by affecting patient behavior or by causing a particular treatment to be administered. For example, a therapy of outdoor aerobic exercise may be employed to achieve a goal of getting more sleep, improving aerobic fitness, or get more sunshine. Thus, the relationship between each therapy entity and goal entities is one to many. A therapy is associated with specific presenting symptoms, and is something the system employs to alleviate, medicate, mediate, or manage a particular symptom, or address a care need. Each therapy has one or more measures associated with it. Thus the relationship between therapy entities and measures is one to many.

Measures—data metric collected from a care recipient or care giver. Measures can be presented as questions, with the answer stored as a metric. They can be collected via devices, such as "Internet of Things" devices—such as Bluetooth scales. Measures provide the data to accomplish the following:

Identify trends related to goals or care needs;
Identify the effectiveness of therapies for a care recipient, or grouping of recipients;
Identify trends and analytics of measures combined with EMR data (e.g., decline in restroom usage correlates with higher rates of urinary tract infections).
Identify at risk recipients and alert care givers a measurement entity may be a distinct entity in a measurement entity level of the care matrix, or one or more measures may be directly associated with a particular goal or therapy entity. A particular measure entity may be associated with one or many therapy entities.

In summary, the care matrix is defined in five levels, and this level of knowledge differentiation provides for sufficient inter-level complexity, and medical/treatment domain knowledge separation, to enable the efficient training of AI instances capable of generating patient care regimens, for example in the form of a therapy profile. More or less levels of distinction are within the scope of this disclosure, and may also provide for adequate generation of treatment regimens for domains of patient care needs.

1) Measures—things we ask or measure about a person to track goal outcomes.
2) Care Activities (therapies) affect behavior in the patient to provide care. Activities can have zero to many measures.
3) Care Goals are goals for the care SimpleC provides, and include 1 or more Care Activities.
4) Care Needs (symptoms) describe issues that patients are having and want to address. Care Needs have one or more Care Goals associated with them.
5) Domain—A collection of care needs that server a type of population In one example of a care need domain, a population of patients suffers from one or more disorders that negatively impact their memory, and a Memory Care Domain is provided. This Memory Care Domain may have a variety of symptoms, such as sleeps too much, sleeps too little, or irregular sleep, suffers from anxiety, and eats infrequently or irregularly. For the care need, or symptom, related to sleep, there may be a variety of goals, such as sleep more, sleep less, sleep on a schedule, etc. For the care goal of sleep less, a related therapy may be an engaging activity that automatically plays for the patient periodically throughout the day—something that keeps the patient upbeat throughout the day.

In various embodiments, therapies are automatically delivered to care recipients based on, among other things, an artificial intelligence analysis of a patients domain, care needs (symptoms), care goals (therapies), and one or more measures, based on the care recipients diagnosis, or disorder, or assigned domain, and a natural language description of the patients current state. For example, a patient, a patient's family member, a patient's doctor, or a patients care specialist, provides a natural language description in response to an interview about the patient. The artificial intelligence has been trained to receive various phrases of the natural language description and to automatically generate a patient therapy profile including one or more therapies, and potentially one or more associated measures, and a therapy schedule. Measures may then be collected by the automated system, a family member, or a care giver and in each case may be used by the system to evaluate the patients progress through therapy, and how effective the treatment profile is at treating the patients symptoms. Measures may then be used to inform later retraining of AI systems.

The care matrix models domains in order to identify how a system can deliver treatment to accomplish goals for symptoms presenting in patient populations. For example, if the Department of Veterans Affairs engages a system to assist veterans with PTSD, the care matrix process can be utilized to model the symptoms and therapies and measures for each particular domain. Once identified, the therapies and measures can be built and delivered to their patient population automatically by the care matrix system based on an ongoing assessment of the patient.

The patient, or the patients family members, or care takers, can provide the system a new assessment, or description, of the patient based on the patients current state. For example, when a patient with PTSD wakes in the morning, the system may query the patient, "how are you feeling today?" or "how does the patient feel today?" Based on the patients response, and knowledge of the patients ongoing membership in one or more domains, and exhibiting various symptoms within that domain, and the patients ongoing goals associated with those symptoms, the system may automatically generate a therapy profile for that particular patient for that particular day. The patients daily therapy profile may differ from day to day. Profiles need not be generated daily, but may be generated more or less often based on the patients overall care needs.

In one example, the care matrix can be implemented as a structured dataset that is provided as input to a system (e.g., a neural network system, IBM Watson). A system can be configured to accept natural language from care givers or family members to identify symptoms or therapies for a care recipient. As another example, a family member can input "My dad needs to eat on a schedule. He gets agitated when he is confused about the people in his home." Utilizing a trained neural network system, or a trained Watson instance, (i.e. using a trained AI) a system identifies that the care recipient has the care needs of "Eating", "Agitation", and "Confusion". The care giver would be presented with therapies that apply to those care needs, and would be allowed to select the most appropriate therapies to deliver.

FIG. 1 illustrates an exemplary system for providing automated medical care to various populations of patients in accordance with various embodiments. In embodiments, an automated medical care system 102 is capable of generating a therapy plan 104 for a patient 106. The automated medical care system 102 prompts the user with a series of questions 108 as part of an interview. This series of questions 108 may be obtained by a textual question and answer, or a patient 106 or other user may provide a description 110 of the patient 106. Typically users response 110 to the questions 108, whether in a textual narrative or a spoken word narrative, include a long discussion 112 that include one or more relevant phrases 114. The user may be the patient 106, or the user may be a patient's family member or care taker if the presenting symptoms of the patient's 106 disorder preclude the patient from responding to the interview questions 108.

The questions 108 may be posed, and the users answers 110 about the patient 106 may be received, by an interface engine 116. It will be appreciated that the posing of questions 108 and the receipt of responses may be performed by one or more computer processes operating cooperatively, but for simplicity these functions are illustrated as being performed by a single engine 116. The interface engine 116 may pose a series of questions 108 by accessing a question database 126, which may include one or more scripts of questions each associated with a domain, a symptom, a goal, a therapy, or a measure that is known to be associated with the patient 106. The users responses 110 are received by the interface engine 116 via one or more inputs to a computing device (e.g. a mouse, a keyboard, a microphone, a camera, another computer). In embodiments the interface engine 116, or its corollary processes, pass the user responses 110 to an NLP 118 that is capable of extracting various speech components, for example nouns and verb phrases, from the users long form discussion of the patient 106 and stores these phrases and the responses 110 in a data store for example a responses/extracted phrases data store 120. An AI 122, trained in patient care using, for example, a patient care data structure formed based on the care matrix discussed above, obtains or is supplied the extracted phrases 120 and analyzes them. In embodiments the AI 122 is a collection of individually trained AI node instances 124a-n each trained on a particular level aspect of the care matrix. For example, one AI Node 124a may be trained specifically for the domain of "Memory Care Domain," such that it is able to receive extracted phrases and generate a response including one or more symptoms implicated by the extracted phrases 120 (and thereby implicated by the long form discussion response 110 from the user). Another AI Node 124b may be trained specifically for a particular symptom exhibited by patients associated with the Memory Care Domain, for example the "Sleeps Too Much" symptom, and is therefore trained to receive extracted phrases 120 to identify one or more goals that are implicated by the phrases 120. Another AI Node 124n may be trained for a particular goal, such that it may receive the extracted phrases 120, analyze them, and then propose one or more therapies. In other embodiments, a particular symptom AI Node, e.g. AI Node 124b, may automatically associate particular therapy entities based on the goal entities that are the result of a symptom AI Node analysis. The AI 122 thus generates a set of results based on the analysis that include a set of recommended therapies with their associated measures. The AI 122 may output the results of its analysis into a results database 128 in the form of a therapy plan 104, or one or more other processes may take the AI 122 output and format the results into a therapy plan 104.

Figure 2:
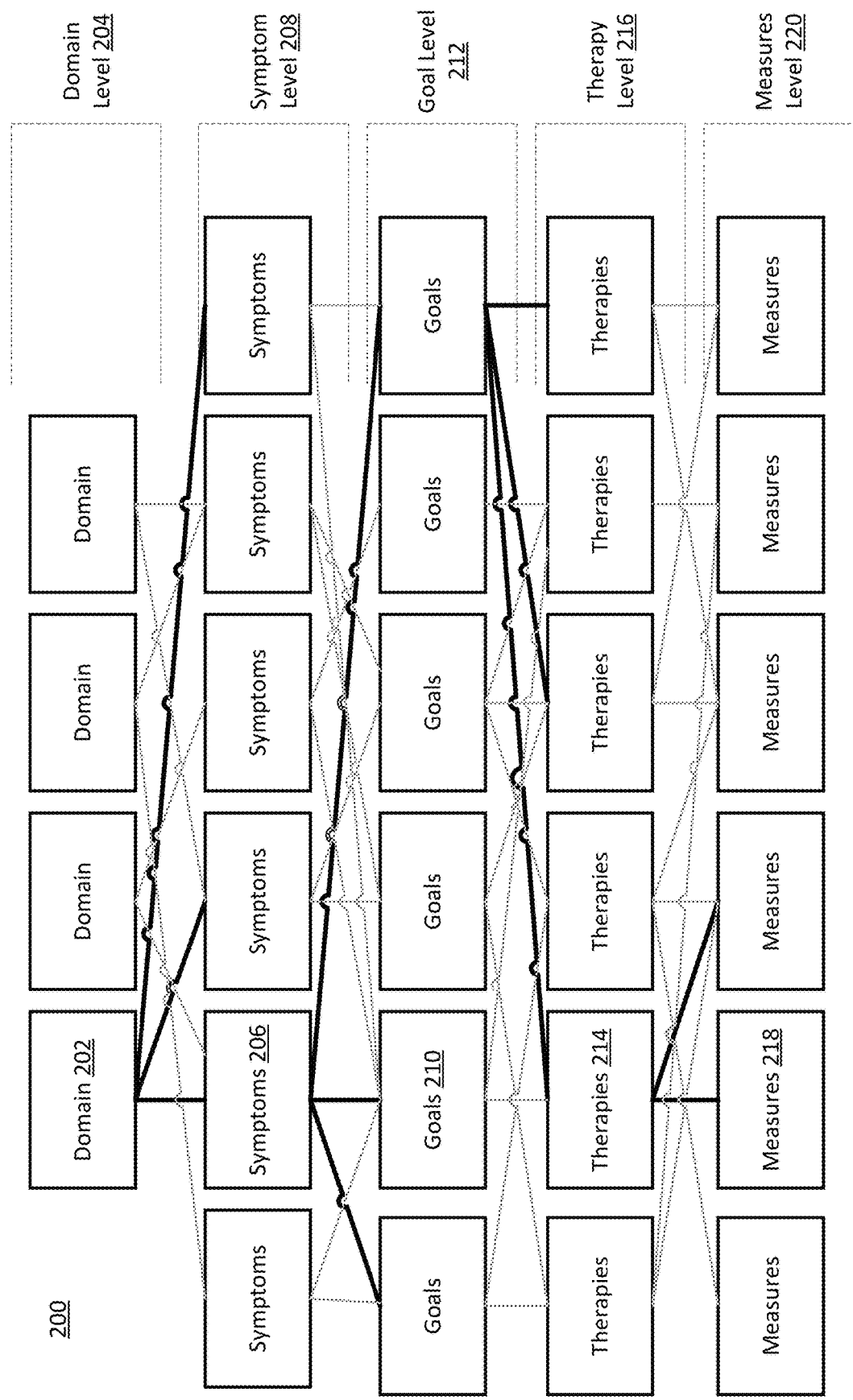
FIG. 2 illustrates a care matrix data structure for training an artificial intelligence to support an automated medical care systems for treating various populations of patients in accordance with various embodiments.

FIG. 2 illustrates a care matrix data structure 200 for training an artificial intelligence to support an automated medical care systems for treating various populations of patients in accordance with various embodiments. The care matrix data structure 200 is organized into five levels as discussed above. The care matrix data structure 200 may be an AI training data set structure or an AI query data structure. The relationship between each entity, e.g. domain 202, within a particular matrix level, e.g. domain level 204, and each entity in an adjacent level, e.g. symptom level 208 is one to many as illustrated. Similarly, each entity within the symptom level 208, e.g. entity 206, has a one to many relationship with entities in each adjacent level, e.g. domain level 204 and goal level 212. In embodiments, there are no direct relationships between entities and other entities that are not in an adjacent level, e.g. there are no direct relationships between symptom 206 and any of the entities in the therapy level 216, e.g. therapy 214, or any of the entities in the measures level 220, e.g. measure 218. In summary, entity relationships between adjacent levels being one to many in both directions, it will be understood that as a general statement the relationships between levels is a many-to-many relationship. As discussed above, this level of knowledge differentiation in a patient care matrix data structure 200 provides for sufficient inter-level complexity, and domain knowledge separation, to enable the efficient training of AI instances capable of generating patient care regimens, for example in the form of a therapy profile. This level of knowledge differentiation in a data structure also enables for accurate and efficient AI processing of patient data to generate therapy profiles. More or less levels of distinction are within the scope of this disclosure, and may also provide for adequate generation of treatment regimens for domains of patient care needs potentially at the expense of efficiency in training or analysis computation. The patent care matrix data structure 200 may be utilized for training a patient care AI such as AI 122. In embodiments each entity, 202, 206, 210, 214, 218 within the care matrix is associated with a set of training data tailored for that instance's purpose. The entity may explicitly include the training data, or the entity may include a reference to training data.

Figure 3:
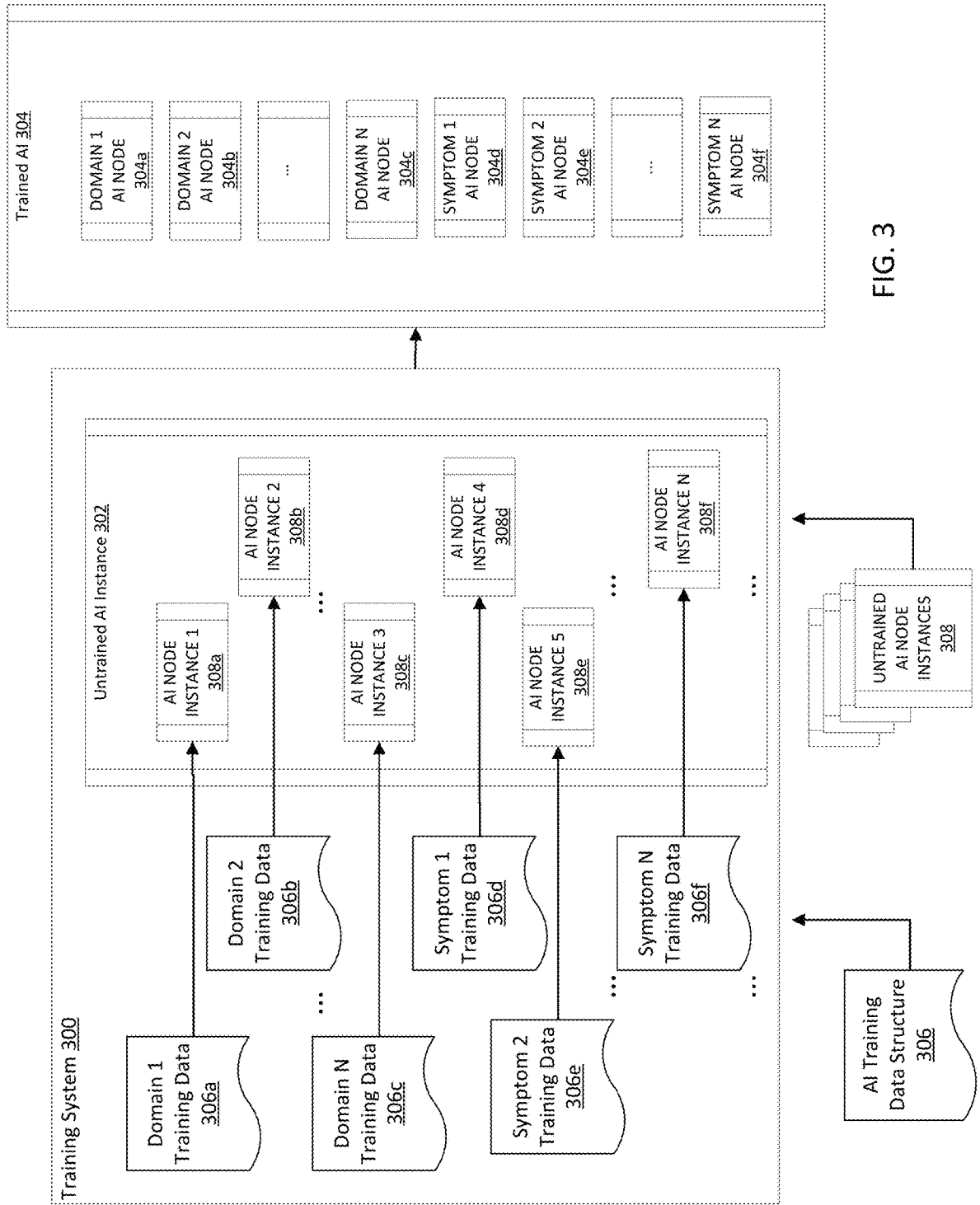
FIG. 3 illustrates a system for training an artificial intelligence in accordance with various embodiments.

FIG. 3 illustrates a system for training an artificial intelligence in accordance with various embodiments. Training system 300 takes in a plurality of untrained AI node instances 308. Each of the plurality of untrained AI node instances 308 may be identical prior to training, or they may differ based on a system designer's appreciation of how well a particular AI instance operates for a particular task (e.g. domain analysis, symptom analysis, a particular symptom analysis). In embodiments the AI instances are based on IBM's Watson technology. In other embodiments, AI instances based on Amazon's AWS technology. Any suitable AI classifier system trained on, e.g. a target corpus (e.g. the English language) may suffice as a particular untrained AI node instance. The training system 300 also takes in an AI training data structure, which in embodiments is the care matrix data structure 200 populated with training data, or with references to training data available to training system 300. An untrained AI instance 302 includes the plurality of untrained AI node instances 308, and is trained according to the requirements of the particular technology employed (Watson, AWS, etc.) using the training data sets 306a-306f contained in or referenced by the AI training data structure 306. The result of training the untrained AI instance 302 with the training sets 306a-f is a trained AI 304 which is formed of a collection of individually trained AI nodes, e.g. Domain 1 AI node 304a, Domain 2 AI node 304b, Domain N AI node 304c, Symptom 1 AI node 304d, Symptom 2 AI node 304e and Sympom N AI node 304f. The trained AI may further include trained AI nodes associated with goals, therapies and measures as will be appreciated based on a full understanding of this disclosure. The resulting trained AI node may be employed to perform automated patient care as AI 122 in patient care system 102.

Figure 4:
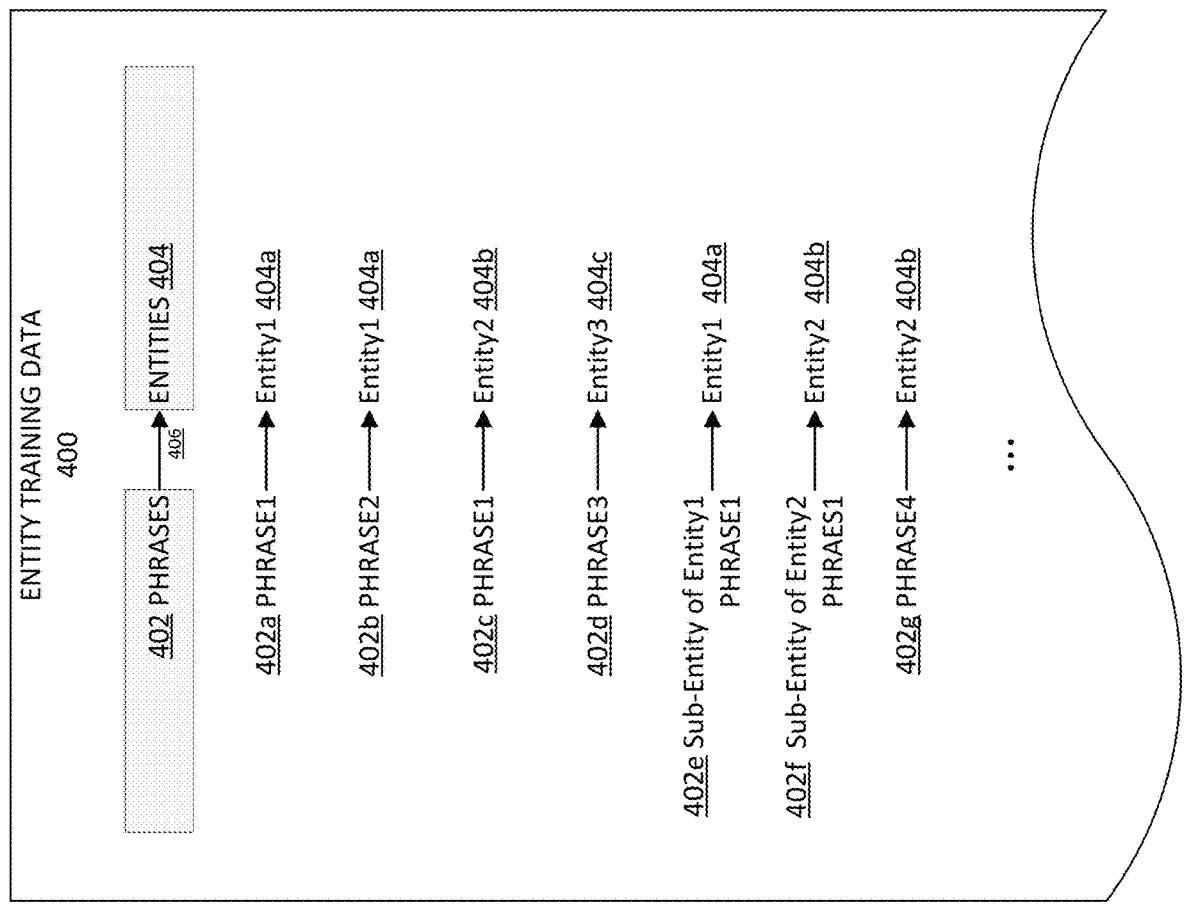
FIG. 4 illustrates training data for training an artificial intelligence in accordance with various embodiments.

FIG. 4 illustrates an exemplary training data structure 400 for training an artificial intelligence in accordance with various embodiments. The exemplary data structure 400 may be used for training any entity of any level of the care matrix 200. Each entity, e.g. entity 202 or 206, is trained to receive input phrases associated with a patients disorder, and to identify one or more sub-entities for further analysis. For example, domain entity 202 is trained to respond to input with an identification of one or more symptom entities (e.g. symptom entity 206). Similarly, symptom entity 206 is trained to respond to input with an identification of one or more goals entities (e.g. goal entity 210). Thus, within the context of this analysis, a symptom entity is a child entity of a domain entity, and a goal entity 210 is a sub entity of both a symptom entity 206 by direct relationship, and is a sub entity of a domain entity 202 by inheritance from a symptom entity 206, e.g. in the context of this analysis goal entity 210 is a sub-entity of a sub-entity of domain entity 202. But for clarity, within the care matrix 200, the relationships are not necessarily hierarchical in nature.

Within an entity training data 400 is a collection of phrases 402 having an association 406 with an entity 404. The PHRASES 404 for entity training data 400 are for training a particular AI node instance in a particular level of the care matrix. Each of the entities 404 are a sub-entity of the entity to be trained (e.g. if data set 400 is for training a domain entity, Entity1 404a and Entity2 404b are symptom entities). A particular phrase may be repeated if it has an association with more than one entities, e.g. PHRASE1 402a is associated with Entity1 404a and PHRASE1 402c is associated with Entity2 404c. The phrases 402 for a particular entity further include phrases of a sub-entity of a sub-entity as described above, but associated with the particular Sub-Entity. Thus, PHRASE1 402e of a Sub-Entity of Entity1 is associated with Entity1 404a. Similarly, PHRASE1 402f of a Sub-Entity of Entity2 is associated here with Entity2. For example, again if this training data is for training a domain AI node entity, Entity1 and Entity2 are symptom entities, and Sub-Entity of Entity1 is a goal entity associated within a domain analysis with Entity1 and Sub-Entity of Entity2 is a goal entity associated within a domain analysis with Entity2.

Figure 5:
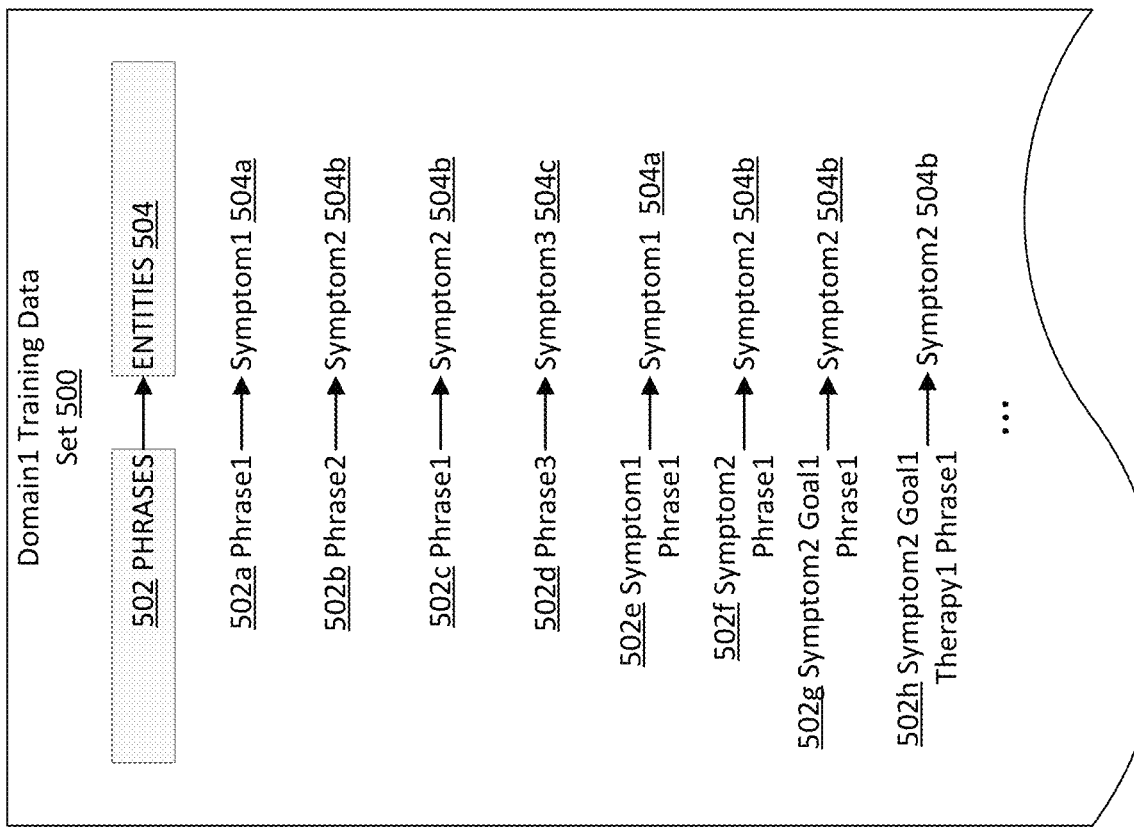
FIG. 5 illustrates training data for training an artificial intelligence in accordance with various embodiments.

FIG. 5 illustrates training data for training a domain AI node in accordance with various embodiments. Domain1 training data set 500 includes a listing of domain level phrases associated with one or more symptoms, e.g. Phrase1 502a, 502c and Phrase2 402b, and Phrase3 402d are domain level phrases associated with symptoms Symptom1 504a, Symptom2 504b, and Symptom3 504c. Symptom1 504a, is associated with Phrase1 502a, and also Symptom1 is associated with a phrase of Symptom1 itself e.g. 502e. Likewise a phrase associated with a goal of a symptom is associated in data set 500 with the symptom. Thus, Phrase1 502g of Symptom2 Goal1 is associated with Symptom2 504b. Likewise a therapy of a goal of a symptom is associated within domain training data set 500 with the its symptom, e.g. Phrase1 502h of Symptom2 Goal1 Therapy1 is associated with Symptom2 504b. Domain level phrases, such as 502a, 502b, 502c, 502d, may include the names of the symptoms associated with the domain, a description of the associated symptom, and one or more hint phrases of the symptom. The description phrases of an associated symptom may themselves be the product of extracting phrases from a long form textual description of the symptom. This may be entered explicitly by a care specialist, or may be taken from a medical or therapy related textual description of the symptom or known concerns associated with the symptom.

Figure 6:
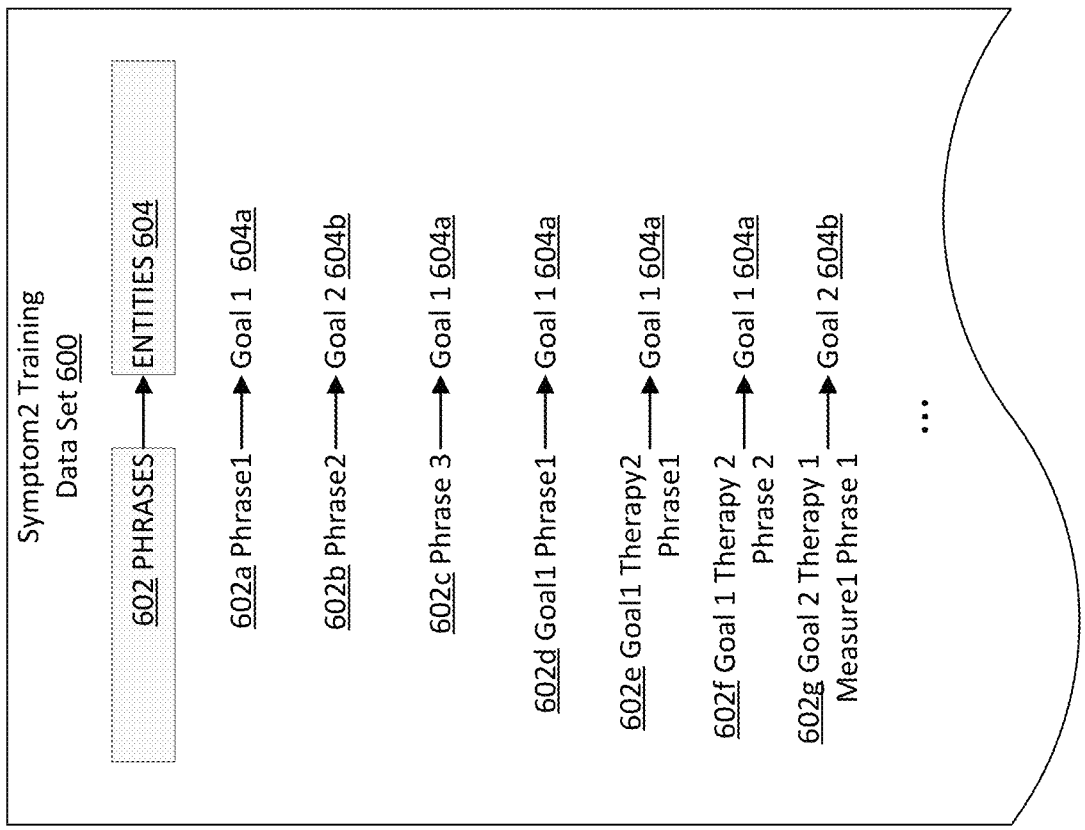
FIG. 6 illustrates training data for training an artificial intelligence in accordance with various embodiments.

FIG. 6 illustrates training data for training an artificial intelligence in accordance with various embodiments. Symptom2 training data set 600 includes a listing of symptom level phrases associated with one or more goals, e.g. Phrase1 602a, Phrase2 602b, and Phrase3 602c are symptom level phrases associated with goals Goal1 604a, Goal22 604b. Goal1 604a, is associated with Phrase1 602a, and also Goal1 is associated with a phrase of Goal1 itself e.g. Phrase 602d. Likewise a phrase associated with a therapy of a goal is associated in data set 600 with the goal. Thus, Phrase1 602d of Goal1 Therapy2 is associated with Goal1 504a. Likewise phrases of a measure associated with a therapy of a goal of a symptom is associated within domain training data set 600 with its goal, e.g. Phrase1 602h of Symptom2 Goal1 Therapy1 Measure1 is associated with Goal2 604b. Symptom level phrases, such as 602a, 602b, 602c, may include the names of the goals associated with Symptom2, a description of the associated goal, and one or more hint phrases of the goal. The description phrases of an associated goal may themselves be the product of extracting phrases (e.g. noun and verb phrases, or other like tokens) from a long form textual description of the goal. This may be entered explicitly by a care specialist, or may be taken from a medical or therapy related textual description of the goal or known concerns associated with the goal. For clarity, all of the PHRASES 602 of Data set 600 will appear in data set 500 having an association with Symptom2 504b.

Figure 7:
FIG. 7 illustrates a flow chart of an example method for training an entity in accordance with various embodiments.

FIG. 7 illustrates a flow chart 700 of an example method for training an entity in accordance with various embodiments. First, entity training data is accessed 702, e.g. entity training data 400, 500 or 600. If this is a first instance of creatinian an entity training data, then an entity training data is created at step 702. A child-entity name (e.g. if entity is to be trained is a domain, the a child entity name is a name of a symptom) is added to the training data at 704 and an association to the child-entity ID is made at 706. Child-entity hint phrases are added in step 708, and an association to the child-entity ID is made at 710. Child-entity hint phrases are known phrases that are intended to be associated with a specific child-entity, but not found in a description of the child-entity. These hint phrases may be added responsive to evaluations of the accuracy and efficiency and effectiveness of an AI in responding to particular phrases. At 712, a natural language processor, such as Apache OpenNLP, is employed to generate phrases from a description of a child-entity, and these phrases are added at 714. At 716 each generated phrase added in step 714 is associated with the child entity. At step 718, all of the phrases associated with each sub-child-entity of the child-entity added in step 704 is added to the training data, and at 720 an association is made between the phrases added in step 718 and the child-entity (e.g. a goal is a child entity of a symptom child entity and in a domain data training set is associated with the symptom entity). At step 722 steps 704-720 are repeated for each child-entity associated with the entity to be trained. At step 724 an untrained AI instance is trained with the entity training data to obtain a trained AI entity node, for example using training system 300.

Figure 8:
FIG. 8 illustrates a flow chart of an example method for training a symptom entity in accordance with various embodiments.

FIG. 8 illustrates a flow chart 800 of an example method for training Symptom_x entity in accordance with various embodiments. In step 802 the Symptom_x training data is accessed, and, a goal Goal_n name is added to the Symptom_x training data at 804. Goal_n's name is associated with Goal_n entity ID at 806. Goal_n hint phrases are added to the training data at 808 and associated with Goal_n entity ID at 810. NLP is employed to generate Goal_n description phrases from a description of Goal_n at 812 and each generated Goal_n phrase is added to the training data for Symptom_x at 814. Each Goal_n description phrase is associated with Goal_n entity ID at 816. At 818 for each therapy associated with Goal_n all associated therapy training phrases may be added to the training phrases for Symptom_x and if so an association is made to Goal_n at 820. At 822, steps 802-820 are repeated for each Goal_i, for 0<{i,n}<N, until all N goals associated with Symptom_x are added to the training set each with an association to a respective Goal_i. At 824, an untrained AI node instance is trained with Symptom_x training data to obtain a symptom trained AI node.

Figure 9:
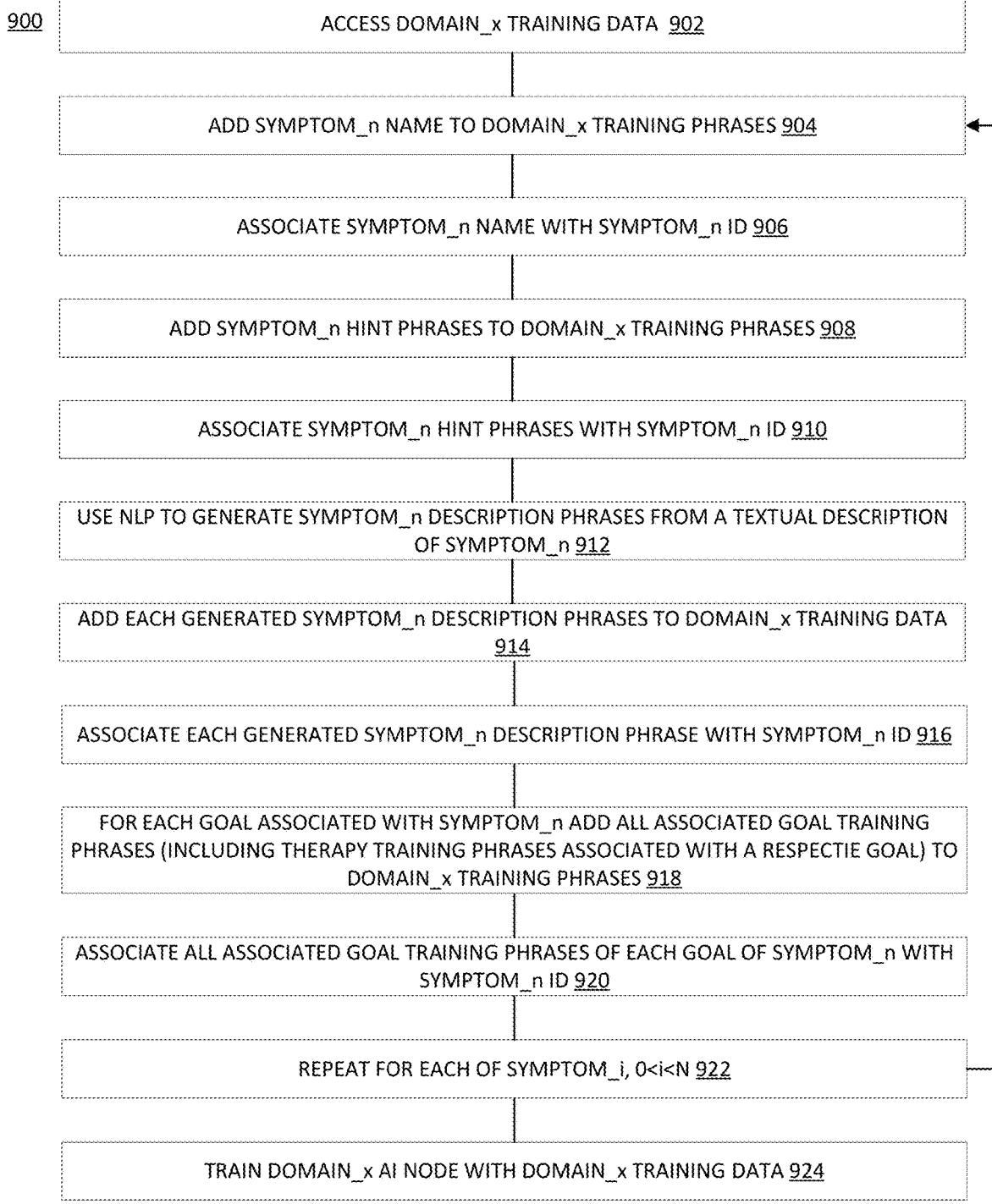
FIG. 9 illustrates a flow chart of an example method for training a domain entity in accordance with various embodiments.

FIG. 9 illustrates a flow chart 900 of an example method for training Domain_x entity in accordance with various embodiments. In step 902 the Domain_x training data is accessed, and, a goal Symptom_n name is added to the Domain_x training data at 904. Symptom_n's name is associated with Symptom_n entity ID at 906. Symptom_n hint phrases are added to the training data at 908 and associated with Symptom_n entity ID at 910. NLP is employed to generate Symptom_n description phrases from a description of Symptom_n at 912 and each generated Symptom_n phrase is added to the training data for Domain_x at 914. Each Symptom_n description phrase is associated with Symptom_n entity ID at 916. At 918 for each goal associated with Symptom_n all associated goal training phrases (including therapy and measure phrases if available) may be added to the training phrases for Domain_x and if so an association is made to Symptom_n at 920. At 922, steps 902-920 are repeated for each Symptom_i, for 0<{i,n}<N, until all N symptoms associated with Domain_x are added to the training set each with an association to a respective Symptom_i. At 924, an untrained AI node instance is trained with Domain_x training data to obtain a domain trained AI node.

FIG. 10 illustrates a block diagram of an example system for obtaining results responsive to an input to an entity AI node entity in accordance with various embodiments. In embodiments, a patient's extracted data phrases 1002 (for example phrases 120 obtained by processing a patient description e.g. 110) are supplied to an Entity AI node 1004 to obtain a set of child-entity IDs and an associated probability. The associated probabilities are a weighting assigned to a particular child-entity in light of the evaluated strength of an association between the extracted phrases 1002 and a particular child entity as determined by entity AI node 1004 based on its training. A discriminator 1008 is applied to the results 1006 of the AI's analysis to obtain results 1010. The discriminator 1008 may evaluate the AI analysis results 1006 based on the assigned probabilities, e.g. p>60%, or the discriminator 1008 may select the top three ranked identified child-entities in results 1006, ranked based on the resulting probability or weight assigned to each entity.

FIG. 11 illustrates a block diagram of an example system for obtaining results 1106 of an natural language processor responsive to an input in accordance with various embodiments. A long form description of a patient (e.g. patient behavior, patient needs, or physical symptoms like temperature, cholesterol count) is supplied to a natural language processor 1104 to obtain a collection of extracted phrases 1106. In an embodiment the NLP 1104 is configured to extract nouns and verb phrases, e.g. for "Dad needs to eat on a schedule" may return "Dad", "Eat", and "Eat on Schedule".

Figure 12:
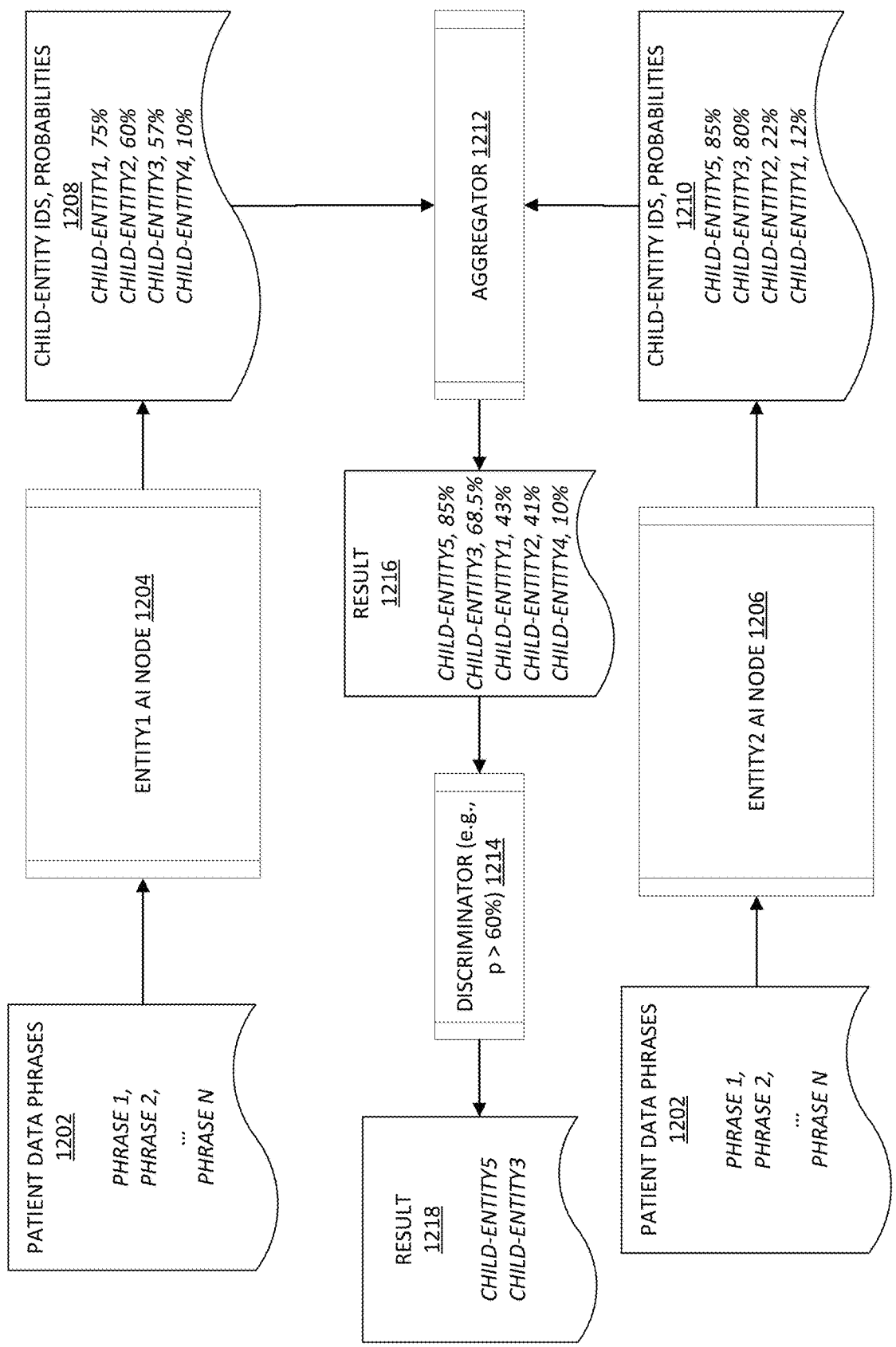
FIG. 12 illustrates a block diagram of an example system for obtaining results responsive to an input to two entity AI nodes entity in accordance with various embodiments.

FIG. 12 illustrates a block diagram of an example system for obtaining results responsive to an input to two entity AI node entities of an AI in accordance with various embodiments. In embodiments, a patient's extracted data phrases 1202 (for example phrases 120 obtained by processing a patient description e.g. 110) are supplied in parallel to an Entity AI nodes 1204 and 1206 to obtain two sets of child-entity IDs 1208 and 1210 each with associated child-entity probabilities. Each set of child-entity IDS 1208 and 1210 may include one or more of the same child-entity IDS by virtue of the one to many relationships in adjacent levels of the care matrix 200. For example each set 1208 and 1210 includes child-entity 1, child-entity2, and child-entity3, but the probabilities associated with each of child-entity 1, child-entity2, and child-entity3 differ in each set 1208 and 1210. The associated probabilities are a weightings assigned to a particular child-entity in light of the evaluated strength of an association between the extracted phrases 1202 and a particular child entity as determined by entity AI nodes 1204, 1206 based on their respective training. The child-entity sets 1208 and 1210 are supplied to an aggregator 1212 in order to obtain a result 1216 including a single set of child-entities and associated weights, wherein each child-entity has one entry. The aggregator 1212 aggregates the scores of the child-entities appearing in each of the child entity sets 1208 and 1210. In embodiments the aggregator averages the scores of a child-entity appearing each set 1208 and 1210. In other embodiments any suitable aggregator function may be employed as is desirable based on domain knowledge regarding the relationships between care matrix entities or a particular patient's profile. A discriminator 1214 is applied to the AI analysis results 1216 of the AI's analysis to obtain results 1218. The discriminator 1214 may evaluate the AI analysis results 1216 based on the assigned probabilities, e.g. p>60%, or the discriminator 1214 may select the top three ranked identified child-entities in results 1216, ranked based on the resulting probability or weight assigned to each entity.

Figure 13A:
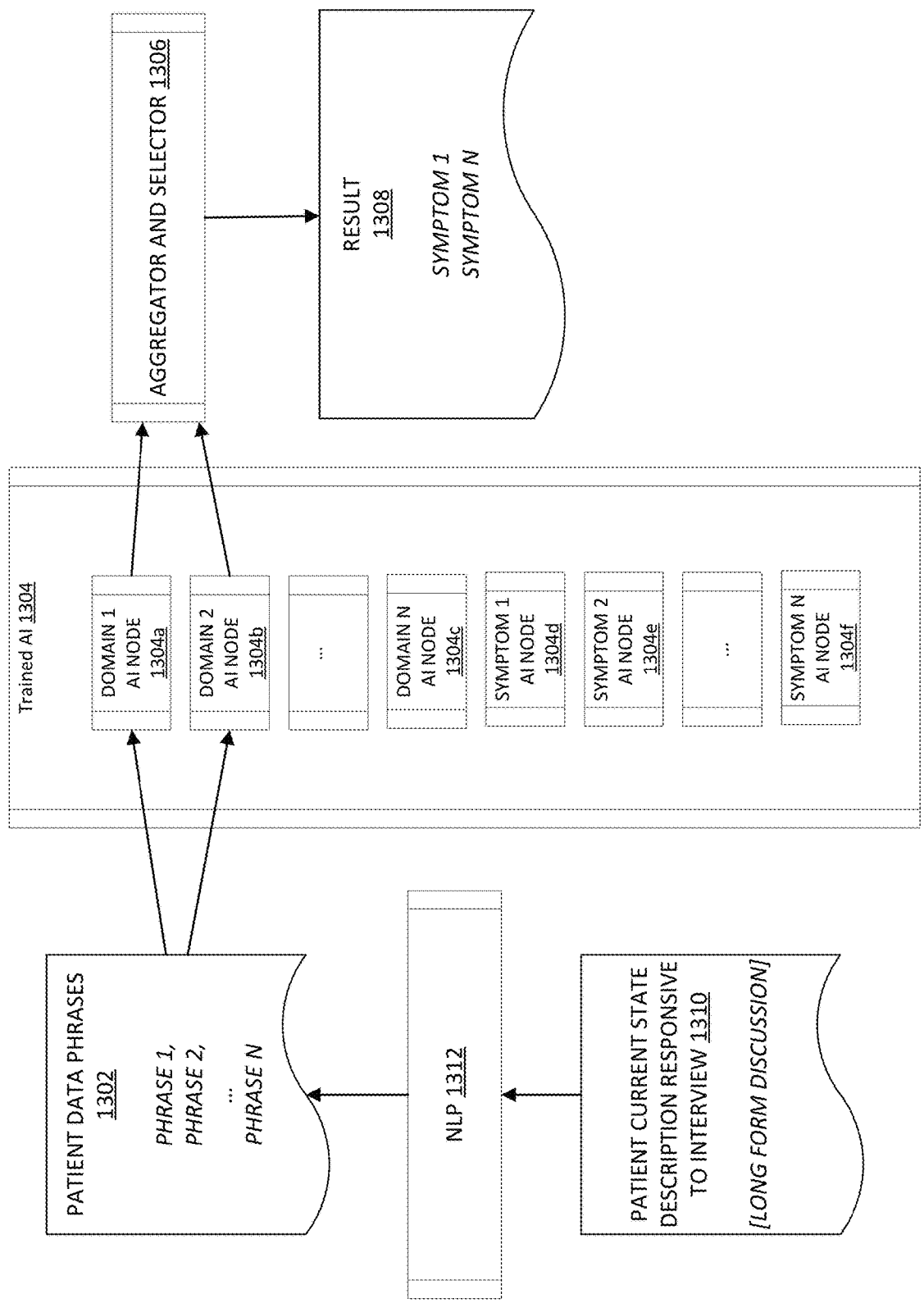
FIG. 13a illustrates a block diagram of an example system for obtaining an intermediate result responsive to an input to patient care system in accordance with various embodiments.

FIG. 13*a* illustrates a block diagram of an example system for obtaining an intermediate result 1308 responsive to an input 1310 to patient care system in accordance with various embodiments. A long form discussion 1310 about the patient, e.g. like description 110, is supplied to an NLP 1312 to obtain extracted patient data phrases 1302. The patient under treatment, e.g. patient 106, by the patient care matrix trained AI 1304 is a member of two domains, domain 1 and domain 2, thus the patients data phrases 1302 are supplied to the trained AI's 1304 domain 1 trained AI node 1304*a* and domain 2 trained AI node 1304*b*. The output of each AI node 1304*a* and 1304*b* is supplied to an aggregator 1306 to obtain intermediate results 1308 including a list of implicated symptoms, implicated by the patient's extracted phrases 1310 according to the trained AI 1304. The intermediate result implications Symptom 1 and Symptom N.

Figure 13B:
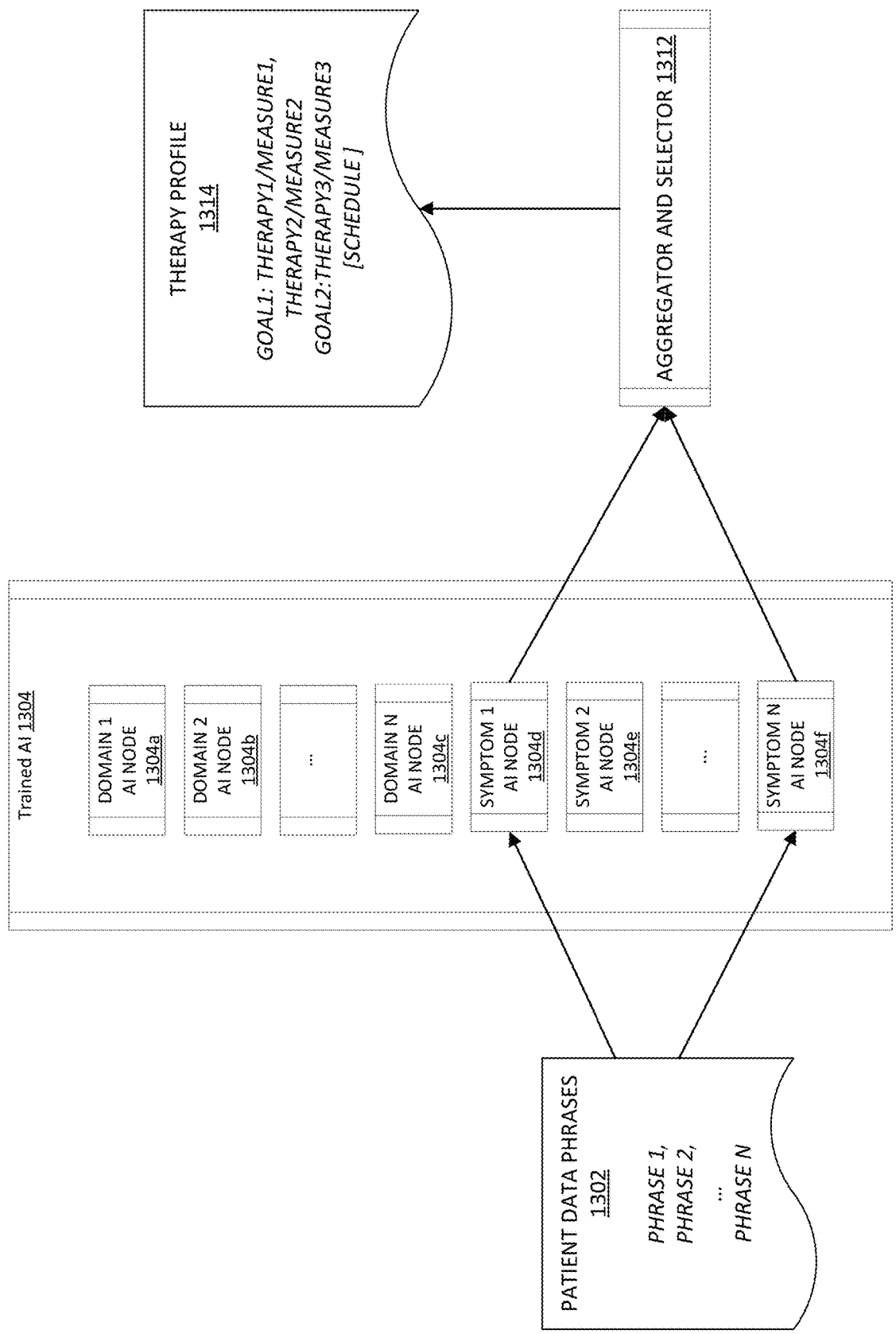
FIG. 13b illustrates a block diagram of an example system for obtaining a result based on an intermediate result responsive to an input to patient care system in accordance with various embodiments.

FIG. 13*b* illustrates a block diagram of an example system for obtaining a result based on an intermediate result responsive to an input to patient care system in accordance with various embodiments. Because the output intermediate result 1308 of the domain level analysis described with reference to FIG. 13*a* above, the patient's extracted data phrases 1302 are now analyzed by trained AI 1304 using Symptom 1 AI node 1304*d* and Symptom N AI node 1304*f*. The results of the analysis by Symptom 1 AI node 1304*d* and Symptom N AI node 1304*f* are supplied to aggregator 1312, which is configured to select the top two goals as ranked by their probabilities, together with their associated therapies, and aggregator 1312 outputs the selected output as part of therapy profile 1314.

Figure 14:
FIG. 14 illustrates a flow chart of an example method for generating a patient therapy profile in accordance with various embodiments.

FIG. 14 illustrates a flow chart of an example method for generating a patient therapy profile in accordance with various embodiments. At 1402 a patient is associated with a domain. The patient, or a caregiver or family member, then is queried with domain related questions at 1404. The responses are supplied to an NLP to obtain extracted phrases at 1406, and the extracted phrases are supplied to a domain AI for analysis at 1408. The domain AI analyzes the extracted phrases and outputs symptoms and associated symptom probabilities, or weights, at 1410. One or more symptoms are selected based on a probability threshold (or ranking) at 1414 as described herein. At 1416, the patients extracted phrases are supplied to one or more symptom trained AI node based on the selected symptoms. At 1418, a set of goals and goal probabilities are generated by each of the symptom trained AI nodes, and the goal probabilities are aggregated at 1420. A set of one or more goals is selected based on a probability threshold at 1422 as described herein. Based on the selected goals at 1424, a set of therapies are assigned to a therapy profile. Optionally at 1426, a set of measures associated with the selected goals along with associated measures are also assigned to the therapy profile.

Figure 15:
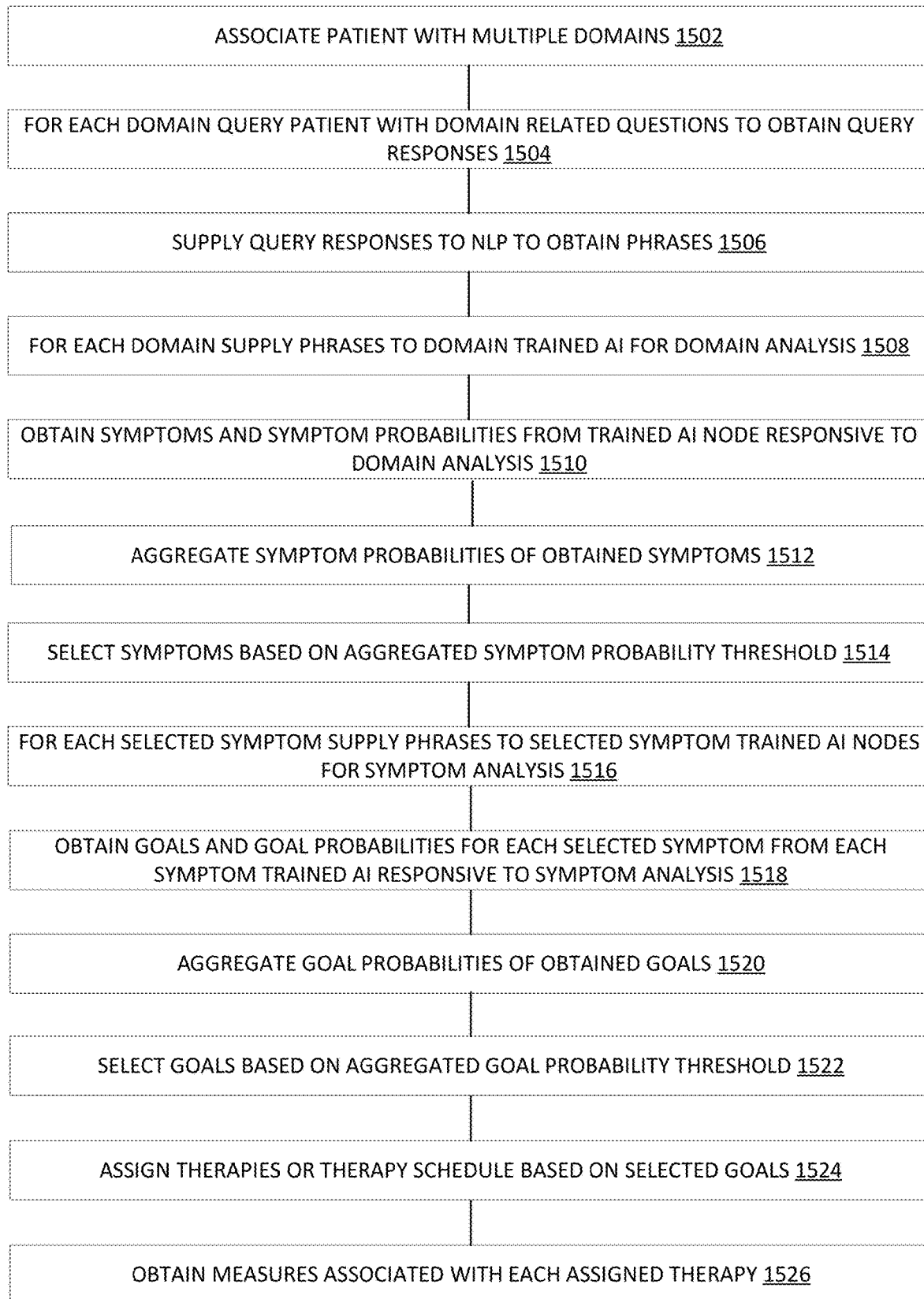
FIG. 15 illustrates a flow chart of an example method for generating a patient therapy profile in accordance with various embodiments.

FIG. 15 illustrates a flow chart of an example method for generating a patient therapy profile in accordance with various embodiments. At 1502 a patient is associated with multiple domains. The patient, or a caregiver or family member, then is queried with domain related questions at 1504. The responses are supplied to an NLP to obtain extracted phrases at 1506, and the extracted phrases are supplied to each domain AI associated with the patient for analysis at 1508. The domain AI analyzes the extracted phrases and outputs symptoms and associated symptom probabilities, or weights, at 1510. The symptom probabilities are aggregated at 1512 to obtain a set of aggregated scores and associated symptoms. One or more symptoms are selected based on a probability threshold (or ranking) of the aggregated scores at 1514 as described herein. At 1516, the patients extracted phrases are supplied to one or more symptom trained AI node based on the selected symptoms. At 1518, a set of goals and goal probabilities are generated by each of the symptom trained AI nodes, and the goal probabilities are aggregated at 1520. A set of one or more goals is selected based on a probability threshold at 1522 as described herein. Based on the selected goals at 1524, a set of therapies are assigned to a therapy profile. Optionally at 1526, a set of measures associated with the selected goals along with associated measures are also assigned to the therapy profile.

In an embodiment in accordance with this disclosure, an artificial intelligence is trained in the domain of alcohol and drug dependency ("ADD"). The artificial intelligence training according to this disclosure results in a trained AI with an understanding of the groupings and frequencies of occurrence of symptoms related to the behavior of ADD population members, the activities of daily living of ADD population members, how ADD population members sleep, and how ADD population members moods change over the course of a period of time, and the problems associated with ADD population member moods. The trained ADD domain AI is able to provide effective patient care by responding to descriptions of the patient throughout the day, and has done so while drastically reducing patient therapy dependence on psychoactive drug prescription. While standard clinical care of ADD patients results in a high percentage (sometimes greater than 90%) of patients being prescribed a psychotropic drug, an exemplary ADD trained AI according to this disclosure understands the implications of a patients on going behavior and provides real time responsive therapy alleviating the need for psychotropic drug prescriptions. This discover has great implications given the U.S. Government's documented recognition that misuse of psychotropic drugs occurs in 99% of patients that receive psychotropic drugs.

For example, in one embodiment, a trained ADD domain AI is consulted by a patient's family member with the statement "my dad is not sleeping well, he misses my mom so he is drinking too much, and he sometimes forgets who I am and it upsets him." The trained AI understands that this sentence contains at least five triggers relevant to ADD domain patients. Standard care for such a patient typically results in the patient being diagnosed as having some form of anxiety and accordingly the patient would be prescribed a psychotropic drug. Instead the trained AI, e.g. AI 122, 304, 1304, 1704, 1726 (trained using a care matrix data structure 200) generates the following analysis: Sleep 24.96%, Confusion 24.9%, Irritable 16.24%, Depression 11.24%, Euphoria 5.82%, Anxiety 4.82%, Dressing 1.15%, Cognitive Activity 1.1%. That is the AI recognized that anxiety's implication based on the patient description is low, and instead of administering a psychotropic drug, appropriate care measures (or therapies) should be employed.

Figure 16:
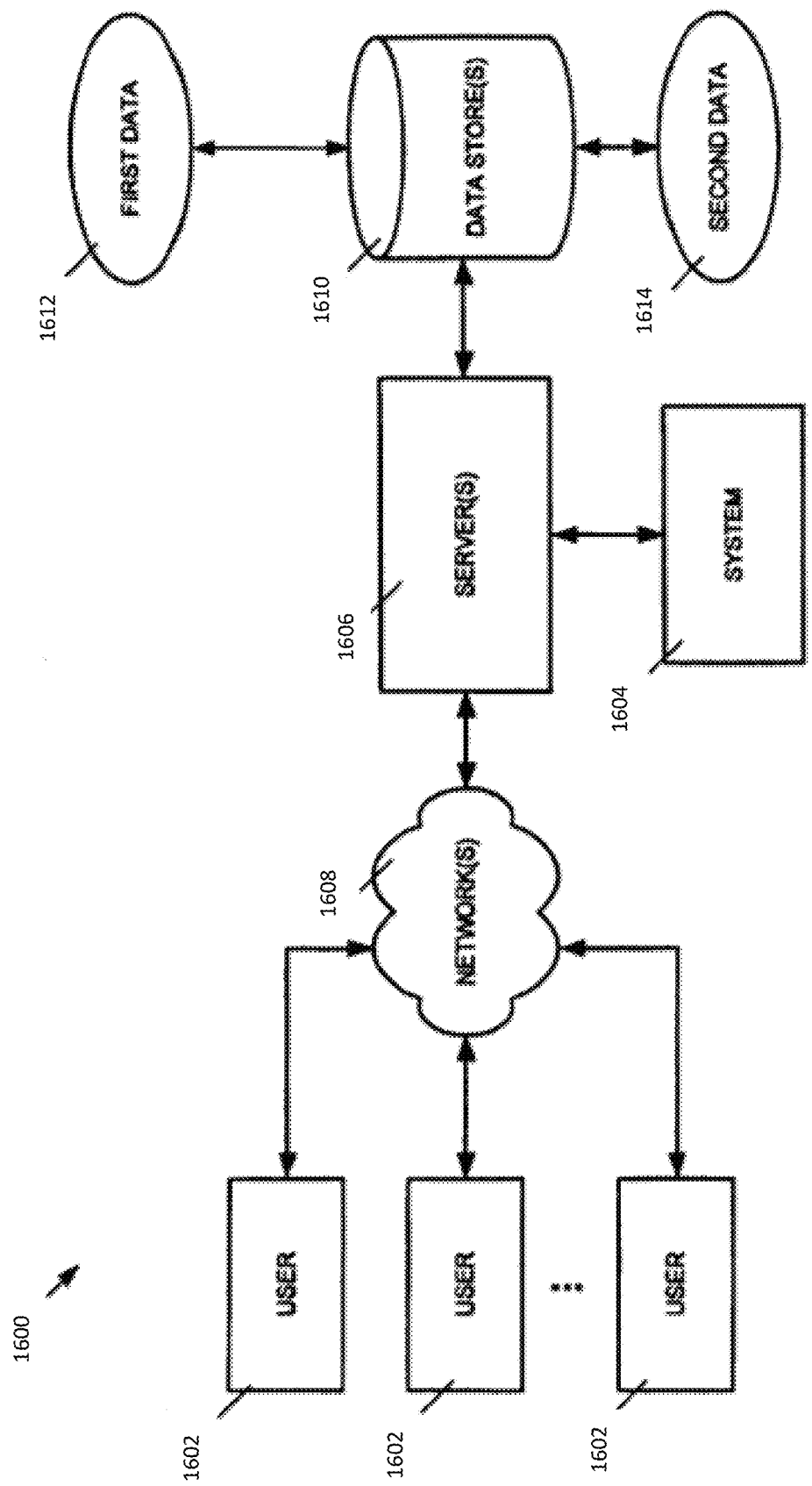
FIG. 16 depicts an example computer-implemented environment.

FIG. 16 depicts at 1600 a computer-implemented environment wherein users 1602 can interact with a system 1604 hosted on one or more servers 1606 through a network 1608. The system 1604 contains software operations or routines. The users 1602 can interact with the system 1604 through a number of ways, such as over one or more networks 1608 via mobile devices, PCs, or other computer devices. One or more servers 1606 accessible through the network(s) 1608 can host system 1604. It should be understood that the system 1604 could also be provided on a standalone computer for access by a user.

Figure 17A:
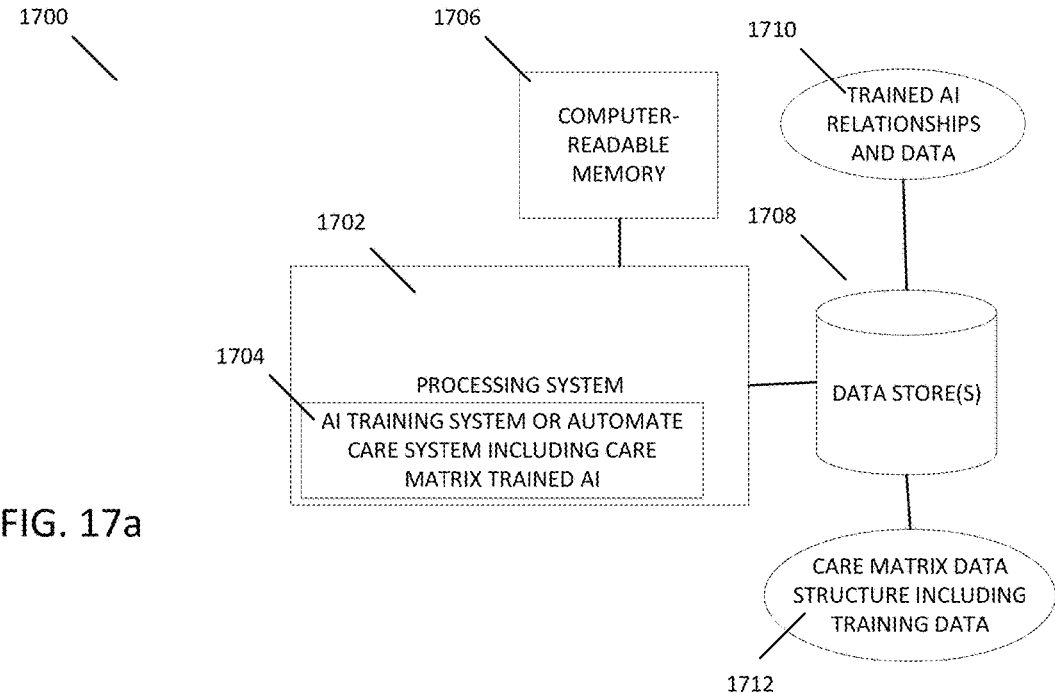
FIGS. 17a-c depict example systems for using in implementing a system.
Figure 17B:
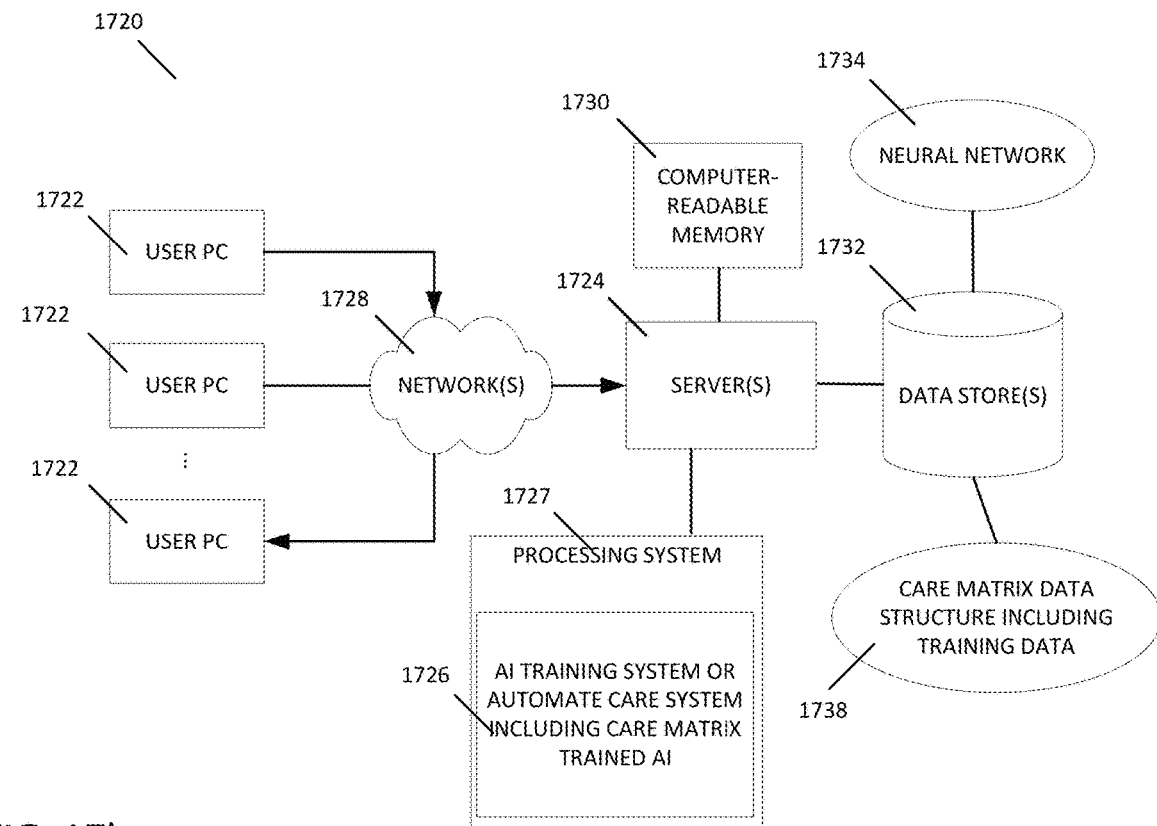
Figure 17C:
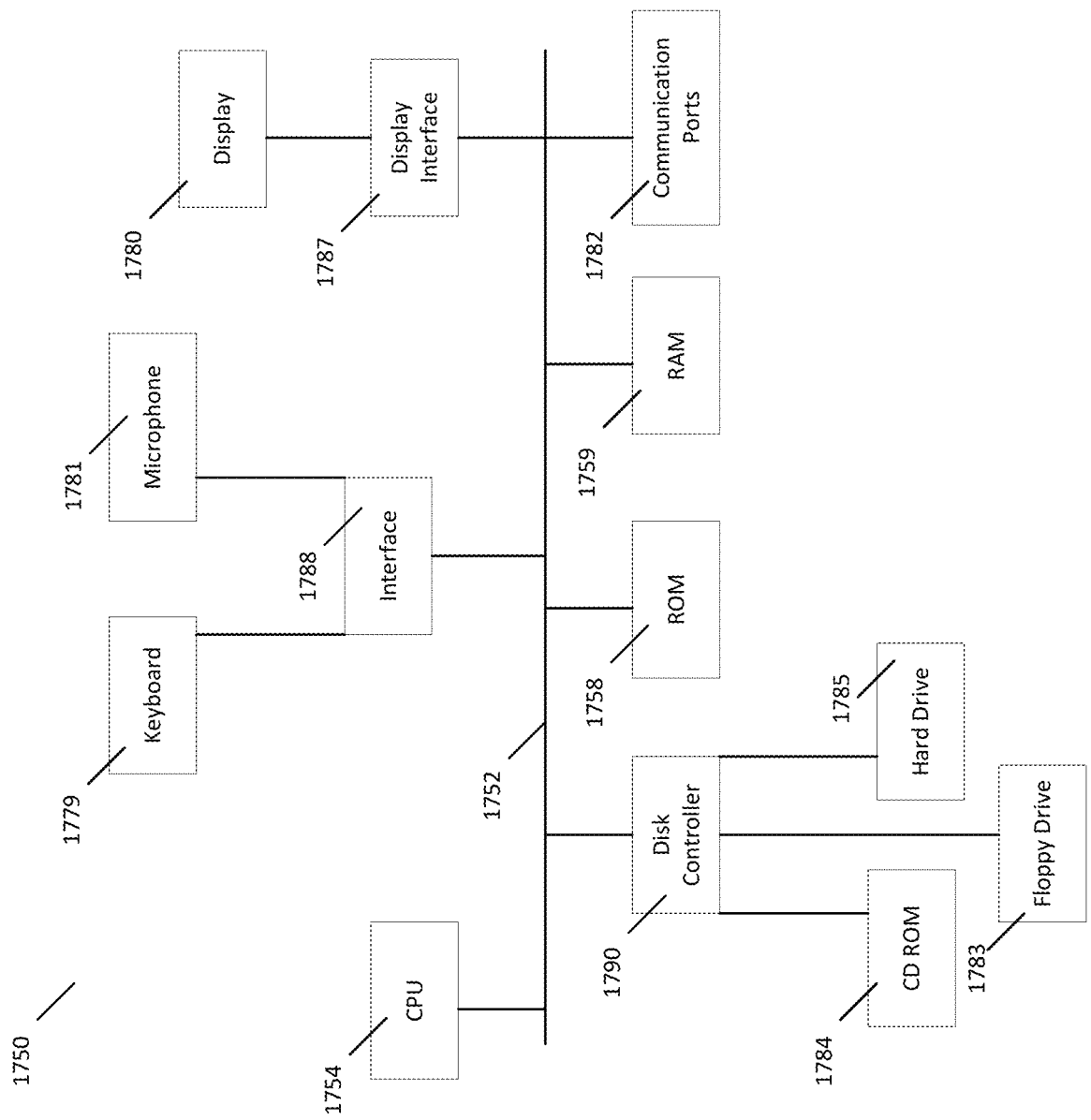

FIGS. 17A-17C depict example systems for use in implementing a system. For example, FIG. 17A depicts an example system 1700 that includes a standalone computer architecture where a processing system 1702 (e.g., one or more computer processors) includes an AI training system or automated care system 1704 being executed on it. The processing system 1702 has access to a non-transitory computer-readable memory 1706 in addition to one or more data stores 1708. The one or more data stores 1708 may contain trained relationships relied upon by an AI during analysis and associated AI data (e.g. metadata, backup data, historical and ancillary data regarding particular analyses) 1710 as well as a care matrix data structure 1712 with training data sets.

FIG. 17B depicts a system that includes a client server architecture. One or more user PCs 1722 accesses one or more servers 1724 running a system 1726 on a processing system 1727 via one or more networks 1728. The one or more servers 1724 may access a non-transitory computer readable memory 1730 as well as one or more data stores 1732. The one or more data stores 1732 may contain trained relationships relied upon by an AI during analysis and associated AI data (e.g. metadata, backup data, historical and ancillary data regarding particular analyses) 1734 as well as a care matrix data structure 1736 with training data sets.

FIG. 17C shows a block diagram of example hardware for a standalone computer architecture 1750, such as the architecture depicted in FIG. 17A, that may be used to contain and/or implement the program instructions of system embodiments of the present disclosure. A bus 1752 may serve as the information highway interconnecting the other illustrated components of the hardware. A processing system 1754 labeled CPU (central processing unit)(e.g., one or more computer processors), may perform calculations and logic operations required to execute a program. A non-transitory computer-readable medium, such as read only memory (ROM) 1756 and random access memory (RAM) 1758, may be in communication with the processing system 1754 and may contain one or more programming instructions. Optionally, program instructions may be stored on a non-transitory computer-readable storage medium such as a magnetic disk, optical disk, recordable memory device, flash memory, or other physical storage medium. Computer instructions may also be communicated via a communication signal, or a modulated carrier wave, e.g., such that the instructions may then be stored on a non-transitory computer-readable storage medium.

A disk controller 1760 interfaces one or more optional disk drives to the system bus 1752. These disk drives may be external or internal floppy disk drives such as 1762, external or internal CD-ROM, CD-R, CD-RW or DVD drives such as 1764, or external or internal hard drives 1766. As indicated above, these various disk drives and disk controllers are optional devices.

A display interface 1768 may permit information from the bus 1752 to be displayed on a display 1770 in audio, graphic, or alphanumeric format. Communication with external devices may optionally occur using various communication ports 1772.

In addition to the standard computer-type components, the hardware may also include data input devices, such as a keyboard 1772, or other input devices 1774, such as a microphone, remote control, pointer, mouse and/or joystick.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

The methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein and may be provided in any suitable language such as C, C++, JAVA, for example, or any other suitable programming language. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

We claim:

1. A method of treating a patient having a disorder associated with a first domain of symptoms exhibited by members of a population of patients having the disorder, comprising:
    training an artificial intelligence (AI) to obtain a trained AI capable of generating a treatment profile for one or more of the members of the population responsive to a set of input phrases by:
        receiving a set of first symptom training phrase associations comprising a plurality of first symptom training phrases each associated with one of a plurality of first symptom treatment goals each of the first symptom treatment goals associated with one or more first therapies for treating a first symptom;

receiving a set of second symptom training phrase associations comprising a plurality of second symptom training phrases each associated with one of a plurality of second symptom treatment goals each of the second symptom treatment goals associated with one or more second therapies for treating a second symptom;

receiving a set of first domain training phrase associations including: (i) the plurality of first symptom training phrases each associated with the first symptom and (ii) the plurality of second symptom training phrases associated with the second symptom;

training a first AI node instance with the set of first domain training phrase associations to obtain a first domain AI node capable of generating, responsive to the set of input phrases, a first set of symptoms to be treated comprising:
  the first symptom or the second symptom; and
  one or more symptom scores, each respective symptom score representative of a strength of a relationship between each of one or more symptom to be treated and the set of input phrases; and training a second AI node instance with the set of first symptom training phrase associations to obtain a first symptom AI node capable of generating, responsive to the set of input phrases, a first set of proposed symptom treatment goals comprising:
  one or more of the plurality of first symptom treatment goals; and
  one or more first symptom goal scores, each respective first symptom goal score representative of a strength of a relationship between each one of the one or more first symptom treatment goals and the set of input phrases; and training a third AI node instance with the set of second symptom training phrase associations to obtain a second symptom AI node instance capable of generating, responsive to the set of input phrases, a second set of proposed symptom treatment goals comprising:
  one or more of the plurality of second symptom treatment goals; and
  one or more second symptom goal scores, each respective second symptom goal score representative of a strength of a relationship between each of the one of the one or more second symptom treatment goals and the set of input phrases; and generating, using the trained AI, a treatment profile of the patient including one or more therapies to be performed to treat a current state of the patient the current state associated with the disorder:

obtaining a description of the current state of the patient;

generating, using a natural language processor, a first set of input phrases based on the description of the current state of the patient;

querying the trained AI using the first set of input phrases as the set on input phrases, wherein querying the trained AI comprises:
  providing the first set of input phrases to the first domain AI node;
  returning, responsive to providing the first set of input phrases to the first domain AI node, the first symptom and the second symptom;
  providing the first set of input phrases to the first symptom AI node;
  returning, from the first symptom AI node responsive to providing the first set of input phrases to the first symptom AI node:
    the first set of proposed symptom treatment goals including
    a first goal and a second goal;
    a first score associated with the first goal; and
    a second score associated with the second goal; and
  providing the first set of input phrases to the second symptom AI node;
  returning, from the second symptom AI node responsive to providing the first set of input phrases to the second symptom AI node:
    the second set of proposed symptom treatment goals including the first goal and a third goal;
    a third score associated with the first goal; and
    a fourth score associated with the third goal; and
  aggregating the first score and the third score to obtain an aggregated score and associating the aggregated score with the first goal;
  selecting the first goal and the third goal when the aggregated score and the fourth score exceed a goal weight threshold and omitting the second goal when the second score does not exceed the threshold; and
  generating the treatment profile including one or more first therapies associated with the first goal and one or third therapies associated with the third goal; and
providing the treatment profile to the patient or the patient's caregiver.

2. The method of treating a patient of claim 1, further comprising:
treating the patient according to the treatment profile by performing the one or more first therapies and the one or more third therapies.

3. The method of treating a patient of claim 1, wherein the treatment profile further includes:
a therapy schedule; and
one or more measures associated with the first goal, the third goal, the first therapies, or the third therapies, wherein treating the patient according to the treatment profile includes:
performing the one or more first therapies and the one or more third therapies according to the therapy schedule; and
collecting measurements based on the one or more measures, the measurements indicative of an effectiveness of the therapy schedule for treating the patient.

4. The method of treating a patient of claim 1, wherein the disorder is further associate with a second domain of symptoms, wherein training an artificial intelligence (AI) to obtain the trained AI capable of generating the treatment profile for one or more of the members of the population responsive to the set of input phrases further includes:
generating a set of third symptom training phrase associations comprising a plurality of third symptom training phrases each associated with one of a plurality of third symptom treatment goals each of the third symptom treatment goals associated with one or more third therapies for treating a third symptom;
generating a set of second domain training phrase associations including:

(i) the plurality of third symptom training phrases each associated with the third symptom and (ii) the plurality of second symptom training phrases associated with the second symptom;

training a fourth AI node instance with the set of second domain training phrase associations to obtain a second domain AI node capable of generating, responsive to the set of input phrases, a second set of symptoms to be treated comprising:

the third symptom or the second symptom; and one or more symptom scores, each respective symptom score representative of a strength of a relationship between each of one or more second symptom to be treated and the set of input phrases; and training a fifth AI node instance with the set of third symptom training phrase associations to obtain a third symptom AI node capable of generating, responsive to the set of input phrases, a third set of proposed symptom treatment goals comprising:

one or more of the plurality of third symptom treatment goals; and one or more third symptom goal scores, each respective third symptom goal score representative of a strength of a relationship between each of the one of the one or more third symptom treatment goals and the set of input phrases; and wherein generating the treatment profile of the patient further includes:

returning, responsive to providing the first set of input phrases to the first domain AI node, a fifth score associated with the first symptom and a sixth score associated with the second symptom;

providing the first set of input phrases to the second domain AI node;

returning, responsive to providing the first set of input phrases to the second domain AI node, the second symptom, the third symptom, a seventh score associated with the second symptom, and an eighth score associated with the third symptom;

aggregating the sixth score and the seventh score to obtain a second aggregated score and associating the second aggregated score with the second symptom; and selecting the first symptom AI node and the second symptom AI for goal analysis when the aggregated score and the fifth score satisfy a domain weight threshold and omitting the third symptom AI node when the eighth score does not satisfy the domain weigh threshold;

wherein the goal analysis includes the step of providing the first set of input phrases to the first symptom AI node; and the step of providing the first set of input phrases to the second symptom AI node.

5. The method of treating a patient of claim 1, further comprising receiving a diagnosis of the patient, the diagnosis associated with the disorder, wherein obtaining the description of the current state of the patient is performed by presenting the patient or a patient caregiver a set of scripted questions and obtaining a free form response to each question of the set of scripted questions, the set of scripted questions selected to elicit response identifying one or more symptoms associated with the first domain, wherein the description includes each free form response to each question of the set of scripted questions.

6. The method of treating a patient of claim 5, wherein generating a first set of input phrases based on the description includes supplying each of the free form responses to a natural language processor for performing natural language processing on each of the free form responses to extract a collection of noun and verb phrases from the description, the collection of noun and verb phrases including one or more first domain training phrases or one or more corollary phrases of at least one of the one or more first domain training phrases.

7. The method of treating a patient of claim 1, wherein the disorder is Alzheimer's disease, further wherein the first domain includes a population of Alzheimer's patients exhibiting a plurality of symptoms associated with a particular stage of Alzheimer's disease, further wherein the plurality of symptoms associated with the first domain is an increasing memory loss and an increase in physical degradation, further wherein the first goal is to delaying memory loss, the second goal is to delaying physical degradation and further wherein the one or more first therapies include one or more memory drills and the third therapies include a physical exercise, further wherein the first domain training phrases include phrases associated with memory loss, physical degradation, delaying memory loss, delaying physical degradation, memory drills, and physical exercise, and wherein the first symptom is increasing memory loss, and the first symptom training phrases include phrases associated with delaying memory loss and memory training, and wherein the second symptom is physical degradation, and the second symptom training phrases include phrases associated with delaying physical degradation and physical exercise.

8. The method of treating a patient of claim 1, wherein the disorder is PTSD, further wherein the domain includes a population of patients exhibiting a plurality of symptoms associated with PTSD, further wherein one of the plurality of symptoms is agitation, further wherein the first goal is alleviating agitation through regularity, further wherein a first therapy associated with alleviating agitation through regularity is eating at a regular time, further wherein a second therapy associated with alleviating agitation through regularity is sleeping at a regular time.

9. The method of treating a patient of claim 1, wherein the AI is based on IBM's Watson technology or Amazon's AWS technology.

10. A method of training an artificial intelligence (AI) instance to treat a plurality of patients each having one of a plurality of disorders each respectively associated with at least one of a plurality domain of symptoms exhibited by members of a population of patients having the disorder, the method comprising:

defining a data structure for use in training the AI to include:

a set of domain data structures, each domain structure associated with a population of patients exhibiting one or more of a plurality of related symptoms;

a set of symptom data structures, each symptom data structure associated with (i) one of a plurality of symptoms exhibited by patients within one or more domains and (ii) one or more goals for managing the one of a plurality of symptoms;

a set of goal data structures, each goal data structure associated with (i) one of the one or more goals and (ii) one or more therapies for managing a symptom associated with the one of the one or more goals; and a set of therapy data structures, each therapy data structure describing a therapy treatment associated with one or more of the goal data structures, wherein each of two or more of the domain data structures respectively include a reference to one of two or more distinct sets of domain training data, further wherein each of two or more of the symptom data structures respectively include a reference to one of two or more distinct sets of symptom training data, further wherein each of two or more of the goal data structures respectively include a reference to one of two or more distinct sets of goal training data; and using the data structure to train an AI instance to obtain a trained treatment AI capable of generating, responsive to a description of a patient's current state, a patient therapy profile, the patient therapy profile including one or more therapies for treating one or more symptoms identified by the AI based on the description of the patient's current state.

11. The method of training an AI instance of claim 10, further comprising populating the data structure with training data by:

defining, within the data structure, a first set of therapies including:
  defining a name of the first therapy;
  defining a description of the first therapy; and
  generating a first set of noun and verb phrases associated with the first therapy based on the description of the first therapy; and
defining, within the data structure, a second set of therapies including:
  defining a name of the second therapy;
  defining a description of the second therapy; and
  generating a second set of noun and verb phrases associated with the first therapy based on the description of the second therapy; and
defining, within the data structure, a first goal including:
  defining a name of the first goal;
  defining a description of the first goal;
  defining one or more hint phrases of the first goal;
  generating a third set of noun and verb phrases associated with the first goal based on the description of the first goal; and
  associating the first goal with first set of noun and verb phrases and the second set of noun and verb phrases; and
defining, within the data structure, a first symptom;
  defining a name of the first symptom;
  defining a description of the first symptom;
  defining one or more hint phrases of the symptom;
  generating a fourth set of noun and verb phrases associated with the first symptom based on the description of the first symptom; and
  associating the first symptom with first set of noun and verb phrases and the second set of noun and verb phrases and the third set of noun and verb phrases; and
defining, within the data structure, a first domain;
  defining a name of the first domain;
  defining a description of the first domain;
  defining one or more hint phrases of the domain;
  generating a fifth set of noun and verb phrases associated with the first domain based on the description of the first domain; and
  associating the first domain with first set of noun and verb phrases and the second set of noun and verb phrases and the third set of noun and verb phrases and the fourth set of noun and verb phrases.

12. The method of training an AI instance of claim 11, further comprising diagnosing a patient with a first disorder associated with a domain; generating a patient therapy profile based on an AI analysis of the domain in order to treat the first disorder; treating symptoms of the patient with one or more therapies according to the patient treatment profile; and obtaining one or more measures indicative of the patient's response to the one or more therapies.

13. The method of training an AI instance of claim 12, wherein the patient therapy profile further includes one or more measures associated with each of the one or more therapies; the method further comprising:

obtaining, responsive to one of the one or more therapies, a new description of the patient's current state;
generating, based on the new description, a new therapy profile;
determining, based in part on the new description and the one or more measures, that the AI instance is not responding to one or more phrases of the description or the new description by returning an expected aspect of the new therapy profile; and
generating one or more hint phrases based on the new description, the one or more hint words having an association with the expected aspect of the new therapy profile;
updating at least one of the sets of domain training data to include the hint phrases and an association between the hint phrases and the expected aspect of the new therapy profile, wherein the expected aspect includes a symptom, a goal, or a therapy.

14. A method of training an artificial intelligence (AI) to obtain a trained AI capable of generating a treatment profile for one or more members of a population responsive to a set of input phrases by:

generating a set of first symptom training phrase associations comprising a plurality of first symptom training phrases each associated with one of a plurality of first symptom treatment goals each of the first symptom treatment goals associated with one or more first therapies for treating a first symptom;
generating a set of second symptom training phrase associations comprising a plurality of second symptom training phrases each associated with one of a plurality of second symptom treatment goals each of the second symptom treatment goals associated with one or more second therapies for treating a second symptom;
generating a set of first domain training phrase associations including: (i) the plurality of first symptom training phrases each associated with the first symptom and (ii) the plurality of second symptom training phrases associated with the second symptom;
training a first AI node instance with the set of first domain training phrase associations to obtain a first domain AI node capable of generating, responsive to the set of input phrases, a first set of symptoms to be treated comprising:
  the first symptom or the second symptom; and
  one or more symptom scores, each respective symptom score representative of a strength of a relationship between each of one or more symptom to be treated and the set of input phrases; and
training a second AI node instance with the set of first symptom training phrase associations to obtain a first symptom AI node capable of generating, responsive to the set of input phrases, a first set of proposed symptom treatment goals comprising:
  one or more of the plurality of first symptom treatment goals; and
  one or more first symptom goal scores, each respective first symptom goal score representative of a strength of a relationship between each one of the one or more first symptom treatment goals and the set of input phrases; and training a third AI node instance with the set of second symptom training phrase associations to obtain a second symptom AI node instance capable of generating, responsive to the set of input phrases, a second set of proposed symptom treatment goals comprising:
one or more of the plurality of second symptom treatment goals; and
one or more second symptom goal scores, each respective second symptom goal score representative of a strength of a relationship between each of the one of the one or more second symptom treatment goals and the set of input phrases.

15. A method of generating, using a trained AI, a treatment profile of a patient that is a member of a domain including one or more therapies to be performed to treat a current state of the patient the current state associated with a disorder:
obtaining a description of the current state of the patient's disorder;
generating, using a natural language processor, a first set of input phrases based on the description of the current state of the patient;
querying the trained AI using the first set of input phrases as the set of input phrases, wherein querying the trained AI comprises:
providing the first set of input phrases to the first domain AI node;
returning, responsive to providing the first set of input phrases to the first domain AI node, the first symptom and the second symptom;
providing the first set of input phrases to the first symptom AI node;
returning, from the first symptom AI node responsive to providing the first set of input phrases to the first symptom AI node:
the first set of proposed symptom treatment goals including a first goal and a second goal;
a first score associated with the first goal; and
a second score associated with the second goal; and
providing the first set of input phrases to the second symptom AI node;
returning, from the second symptom AI node responsive to providing the first set of input phrases to the second symptom AI node:
the second set of proposed symptom treatment goals including the first goal and a third goal;
a third score associated with the first goal; and
a fourth score associated with the third goal; and
aggregating the first score and the third score to obtain an aggregated score and associating the aggregated score with the first goal;
selecting the first goal and the third goal when the aggregated score and the fourth score exceed a goal weight threshold and omitting the second goal when the second score does not exceed the threshold; and
generating the treatment profile including one or more first therapies associated with the first goal and one or third therapies associated with the third goal; and
providing the treatment profile to the patient or the patients caregiver.

16. A system for treating a patient having a disorder associated with a first domain of symptoms exhibited by members of a population of patients having the disorder, comprising:
one or more data stores configured to store training data in an AI training data structure, and patient data in an AI query structure;
a natural language processing engine;
an interface for obtaining the patient data in the form of a description of the current state of the patient;
an artificial intelligence (AI) training engine stored on a non-transitory computer-readable medium and executable by a processor, the AI training engine configured to:
train an AI to obtain a trained AI capable of generating a treatment profile for one or more of the members of the population responsive to a set of input phrases by:
generating a set of first symptom training phrase associations comprising a plurality of first symptom training phrases each associated with one of a plurality of first symptom treatment goals each of the first symptom treatment goals associated with one or more first therapies for treating a first symptom;
generating a set of second symptom training phrase associations comprising a plurality of second symptom training phrases each associated with one of a plurality of second symptom treatment goals each of the second symptom treatment goals associated with one or more second therapies for treating a second symptom;
generating a set of first domain training phrase associations including: (i) the plurality of first symptom training phrases each associated with the first symptom and (ii) the plurality of second symptom training phrases associated with the second symptom;
training a first AI node instance with the set of first domain training phrase associations to obtain a first domain AI node capable of generating, responsive to the set of input phrases, a first set of symptoms to be treated comprising:
the first symptom or the second symptom; and
one or more symptom scores, each respective symptom score representative of a strength of a relationship between each of one or more symptom to be treated and the set of input phrases; and
training a second AI node instance with the set of first symptom
training phrase associations to obtain a first symptom AI node capable of generating, responsive to the set of input phrases, a first set of proposed symptom treatment goals comprising:
one or more of the plurality of first symptom treatment goals; and
one or more first symptom goal scores, each respective first symptom goal score representative of a strength of a relationship between each one of the one or more first symptom treatment goals and the set of input phrases; and
training a third AI node instance with the set of second symptom
training phrase associations to obtain a second symptom AI node instance capable of generating, responsive to the set of input phrases, a second set of proposed symptom treatment goals comprising:
one or more of the plurality of second symptom treatment goals; and one or more second symptom goal scores, each respective second symptom goal score representative of a strength of a relationship between each of the one of the one or more second symptom treatment goals and the set of input phrases; and a patient therapy profile generation engine, including the trained AI, stored on a non-transitory computer-readable medium and executable by a processor, the patient therapy profile generation engine configured to:

generate, using the trained AI, a treatment profile of the patient including one or more therapies to be performed to treat a current state of the patient the current state associated with the disorder by:

obtaining the description of the current state of the patient;

generating, using a natural language processor, a first set of input phrases based on the description of the current state of the patient;

querying the trained AI to obtain using the first set of input phrases as the set on input phrases, wherein querying the trained AI comprises:

providing the first set of input phrases to the first domain AI node;

returning, responsive to providing the first set of input phrases to the first domain AI node, the first symptom and the second symptom;

providing the first set of input phrases to the first symptom AI node;

returning, from the first symptom AI node responsive to providing the first set of input phrases to the first symptom AI node:

the first set of proposed symptom treatment goals including a first goal and a second goal;

a first score associated with the first goal; and a second score associated with the second goal; and providing the first set of input phrases to the second symptom AI node;

returning, from the second symptom AI node responsive to providing the first set of input phrases to the second symptom AI node:

the second set of proposed symptom treatment goals including the first goal and a third goal;

a third score associated with the first goal; and a fourth score associated with the third goal; and aggregating the first score and the third score to obtain an aggregated score and associating the aggregated score with the first goal;

selecting the first goal and the third goal when the aggregated score and the fourth score exceed a goal weight threshold and omitting the second goal when the second score does not exceed the threshold; and generating the treatment profile including one or more first therapies associated with the first goal and one or third therapies associated with the third goal; and providing the treatment profile to the patient or the patients caregiver.

17. The system of claim 16, wherein the first symptom training phrases include various phrases associated with the symptom, the goals associated with the symptom, and the therapies associated with the goals associated with the symptom, wherein the natural language processor generates one or more the first symptom training phrases based on a long form natural language description of each of the symptom, the goals associated with the symptom, and the therapies associated with the goals associated with the symptom.

18. The system of claim 17, wherein the first domain training phrases include various phrases associated with the domain, the symptoms associated with the domain, the goals associated with the symptoms associated with the domain, and the therapies associated with the goals associated with the symptoms associated with the domain, wherein the natural language processor generates one or more the first domain training phrases based on a long form natural language description of each of the domain, the symptoms associated with the domain, the goals associated with the symptoms associated with the domain, and the therapies associated with the goals associated with the symptoms associated with the domain.

19. The system of claim 18, further comprising:

generating instructions for treating the patient according to the treatment profile by performing the one or more first therapies and the one or more third therapies.

20. The system claim 19, wherein the treatment profile further includes:

a therapy schedule; and one or more measures associated with the first goal, the third goal, the first therapies, or the third therapies, wherein treating the patient according to the treatment profile includes:

performing the one or more first therapies and the one or more third therapies according to the therapy schedule; and collecting measurements based on the one or more measures, the measurements indicative of an effectiveness of the therapy schedule for treating the patient.

* * * * *

UNITED STATES PATENT AND TRADEMARK OFFICE
CERTIFICATE OF CORRECTION

| | | |
|---|---|---|
| PATENT NO. | : 12,020,818 B1 | |
| APPLICATION NO. | : 17/832744 | |
| DATED | : June 25, 2024 | |
| INVENTOR(S) | : Douglas Nelson et al. | |

It is certified that error appears in the above-identified patent and that said Letters Patent is hereby corrected as shown below:

In the Claims

Column 30, Line 39, Claim 20, delete "claim" and insert -- of claim --

Signed and Sealed this
Eighth Day of October, 2024

Katherine Kelly Vidal
*Director of the United States Patent and Trademark Office*